(12) United States Patent
Ogawa et al.

(10) Patent No.: US 12,235,442 B2
(45) Date of Patent: Feb. 25, 2025

(54) LINE-OF-SIGHT DETECTION DEVICE AND DISPLAY DEVICE

(71) Applicant: SONY GROUP CORPORATION, Tokyo (JP)

(72) Inventors: Ryo Ogawa, Tokyo (JP); Yuki Mamishin, Tokyo (JP); Takuro Noda, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 0 days.

(21) Appl. No.: 18/245,401

(22) PCT Filed: Sep. 2, 2021

(86) PCT No.: PCT/JP2021/032288
§ 371 (c)(1),
(2) Date: Mar. 15, 2023

(87) PCT Pub. No.: WO2022/074973
PCT Pub. Date: Apr. 14, 2022

(65) Prior Publication Data
US 2023/0350197 A1    Nov. 2, 2023

(30) Foreign Application Priority Data

Oct. 5, 2020   (JP) ................... 2020-168764

(51) Int. Cl.
*G06F 3/01*   (2006.01)
*G02B 5/30*   (2006.01)
(Continued)

(52) U.S. Cl.
CPC ....... *G02B 27/0093* (2013.01); *G02B 5/3083* (2013.01); *G02B 5/32* (2013.01)

(58) Field of Classification Search
None
See application file for complete search history.

(56) References Cited

U.S. PATENT DOCUMENTS 11,067,821 B2 *  7/2021  Andreev ............ G02B 27/0093
11,073,903 B1 *  7/2021  Ouderkirk .......... G02B 27/0172
(Continued)

FOREIGN PATENT DOCUMENTS

JP    2005-257278 A    9/2005
JP    2008-102902 A    5/2008
(Continued)

OTHER PUBLICATIONS

International Search Report and Written Opinion of PCT Application No. PCT/JP2021/032288, issued on Nov. 16, 2021, 11 pages of ISRWO.

*Primary Examiner* — Brian M Butcher
(74) *Attorney, Agent, or Firm* — CHIP LAW GROUP

(57) ABSTRACT

A line-of-sight detection device capable of achieving further improvement in line-of-sight detection accuracy, achieving low latency, and achieving low power consumption is provided. A line-of-sight detection device includes an imaging element, an illumination unit that illuminates an eyeball with a plurality of beams of illumination light, an optical element that guides respective beams of reflected light in a plurality of directions from the eyeball caused by the plurality of beams of illumination light to a direction of the imaging element, an optical system that causes the imaging element to non-selectively receive the beams of reflected light in the plurality of directions from the eyeball, and a calculation unit that converts, on the basis of the beams of reflected light in the plurality of directions from the eyeball received by the imaging element, the beams of reflected light into information of eyeball movement and/or positional information of a pupil.

20 Claims, 14 Drawing Sheets

(51) Int. Cl.
G02B 5/32 (2006.01)
G02B 27/00 (2006.01)

(56) References Cited

U.S. PATENT DOCUMENTS

| | | |
|---|---|---|
| 2007/0076958 A1 | 4/2007 | Venkatesh |
| 2017/0082858 A1 | 3/2017 | Klug |
| 2018/0140187 A1 | 5/2018 | Watanabe |
| 2019/0041634 A1 | 2/2019 | Popovich |
| 2019/0286228 A1* | 9/2019 | Sangu .................... G06F 3/011 |
| 2020/0241635 A1 | 7/2020 | Cohen |

FOREIGN PATENT DOCUMENTS

| | | |
|---|---|---|
| JP | 2012-532347 A | 12/2012 |
| JP | 2017-527036 A | 9/2017 |
| JP | 2018-028728 A | 2/2018 |
| JP | 2018-530781 A | 10/2018 |
| JP | 2020-513609 A | 5/2020 |
| WO | WO-2019147677 A1 | 8/2019 |
| WO | 2019/176150 A1 | 9/2019 |

* cited by examiner

FIG. 1
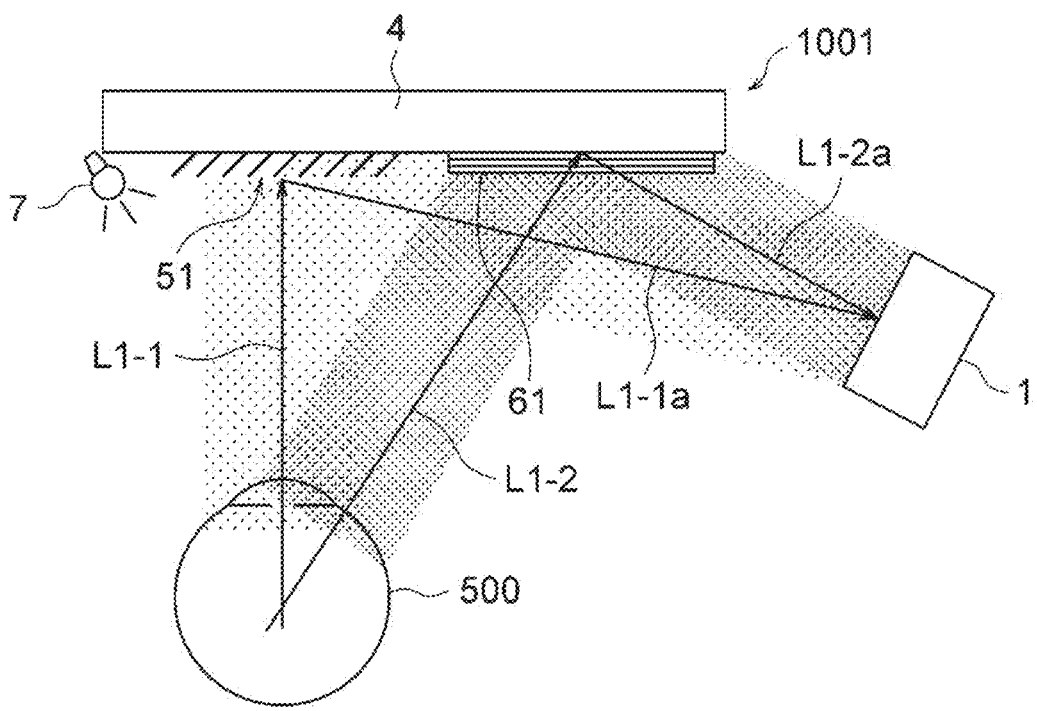
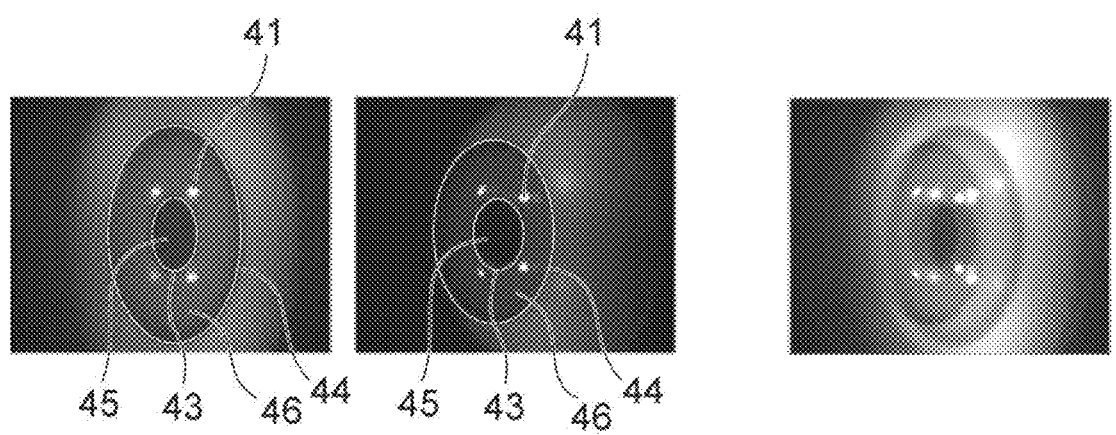
FIG. 2A  FIG. 2B  FIG. 2C

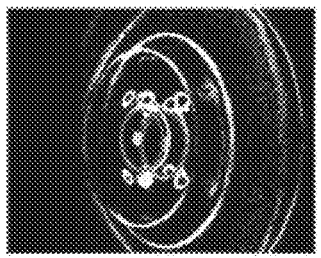
FIG. 3A
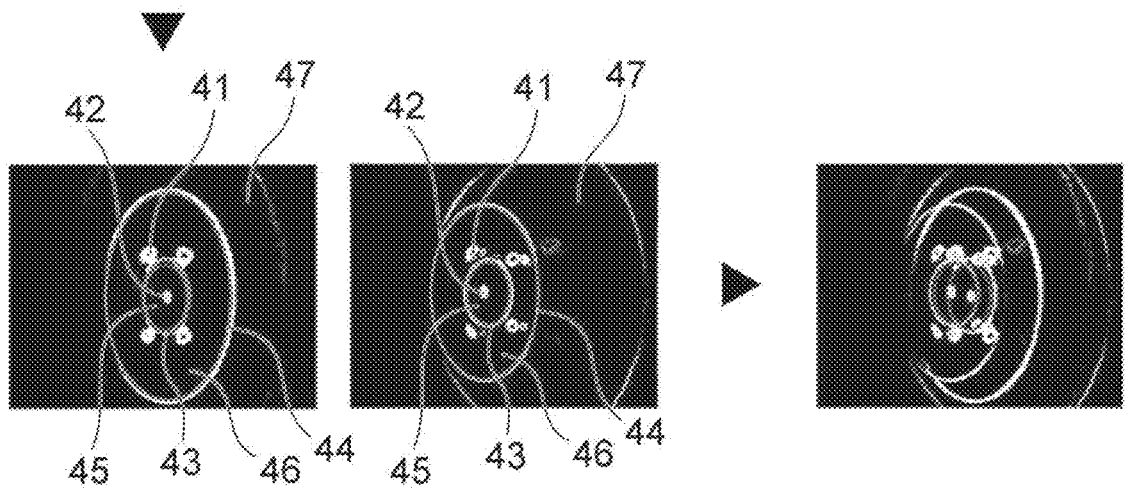
FIG. 3B
FIG. 3C
FIG. 3D

FIG. 5
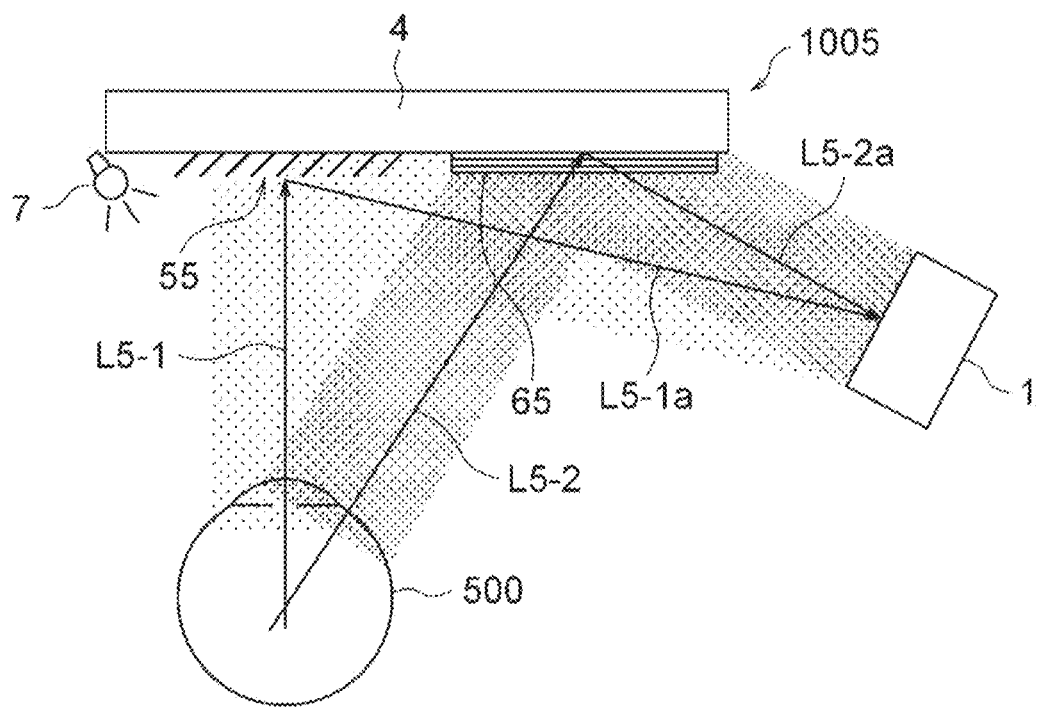
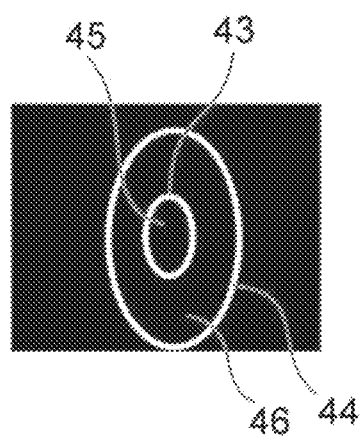
FIG. 6A
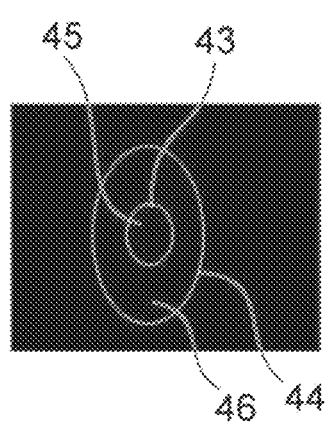
FIG. 6B
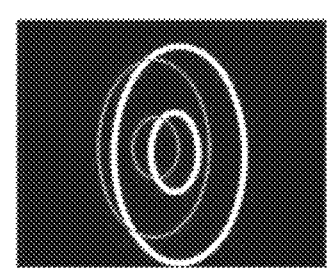
FIG. 6C

FIG. 7
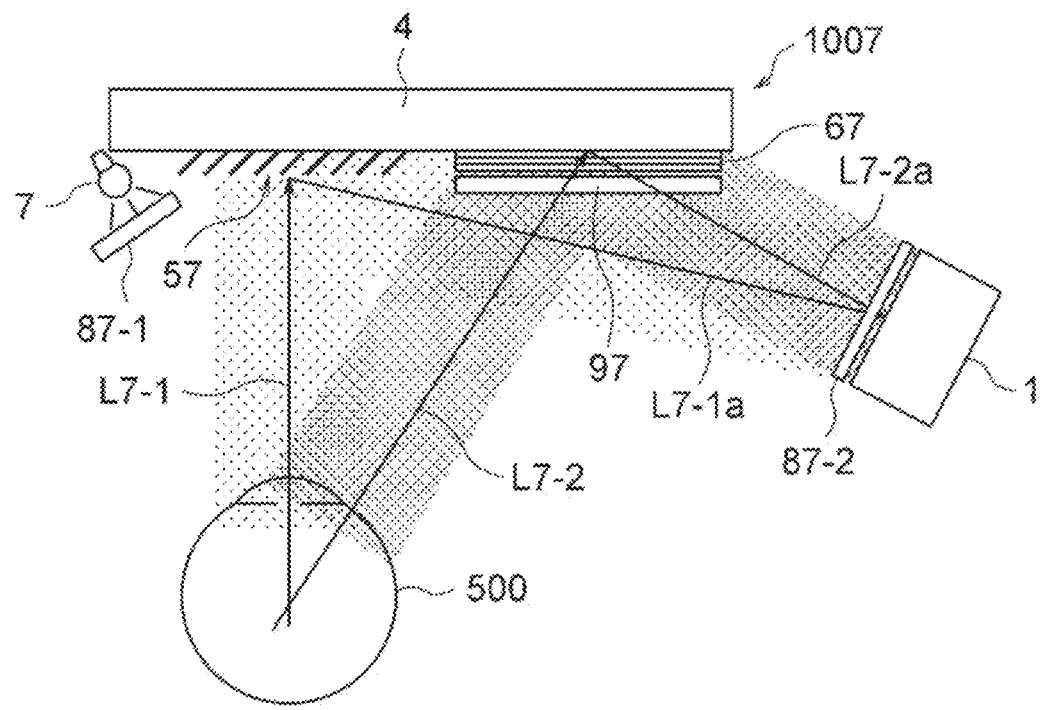
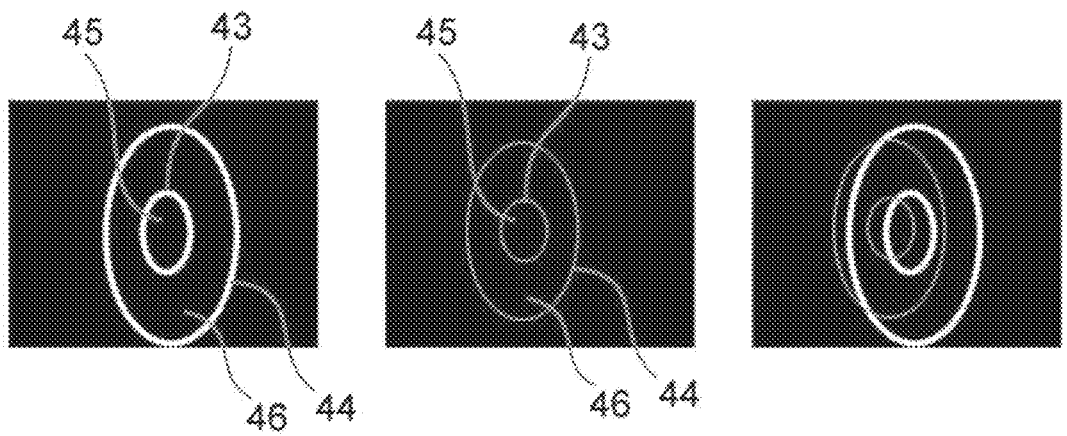
FIG. 8A     FIG. 8B     FIG. 8C

FIG. 9
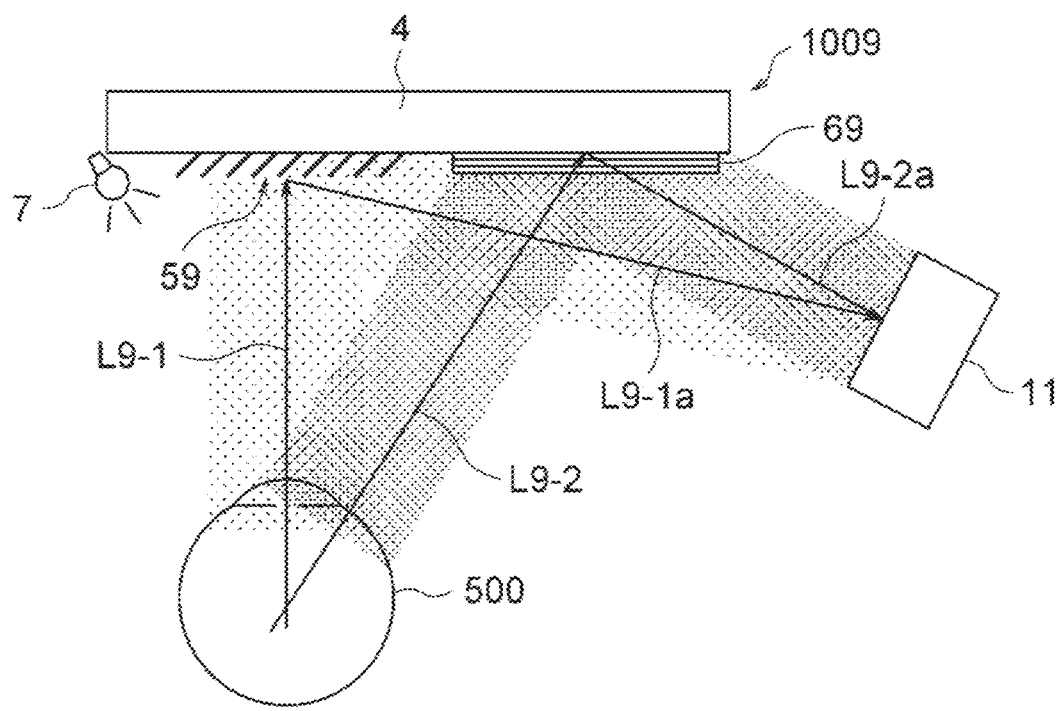
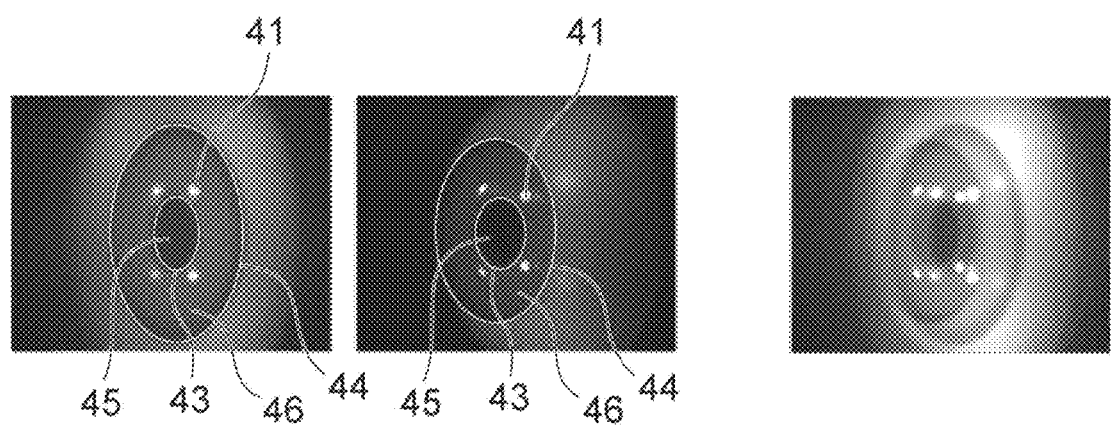
FIG. 10A    FIG. 10B    FIG. 10C

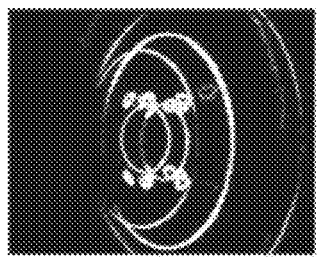
FIG. 11A
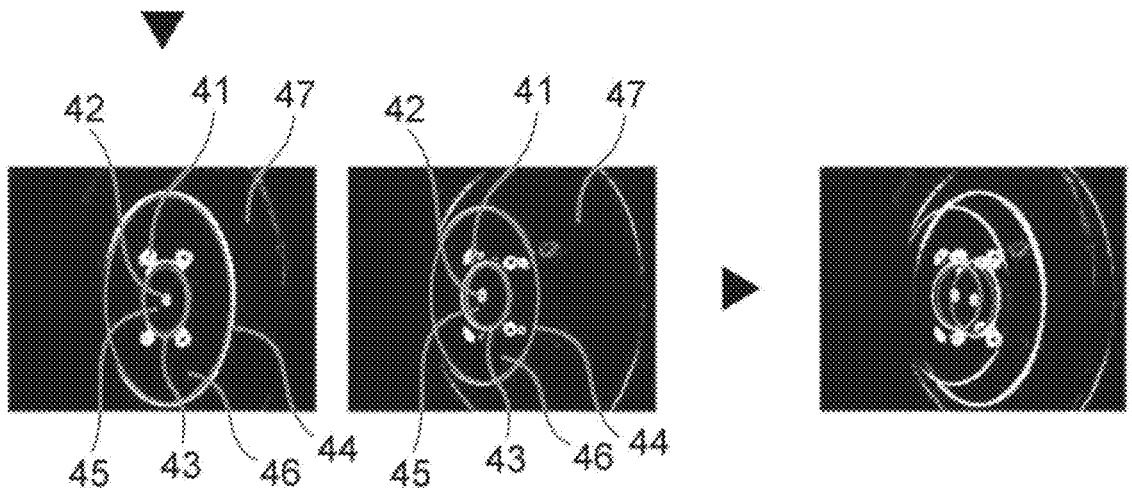
FIG. 11B
FIG. 11C
FIG. 11D

FIG. 15
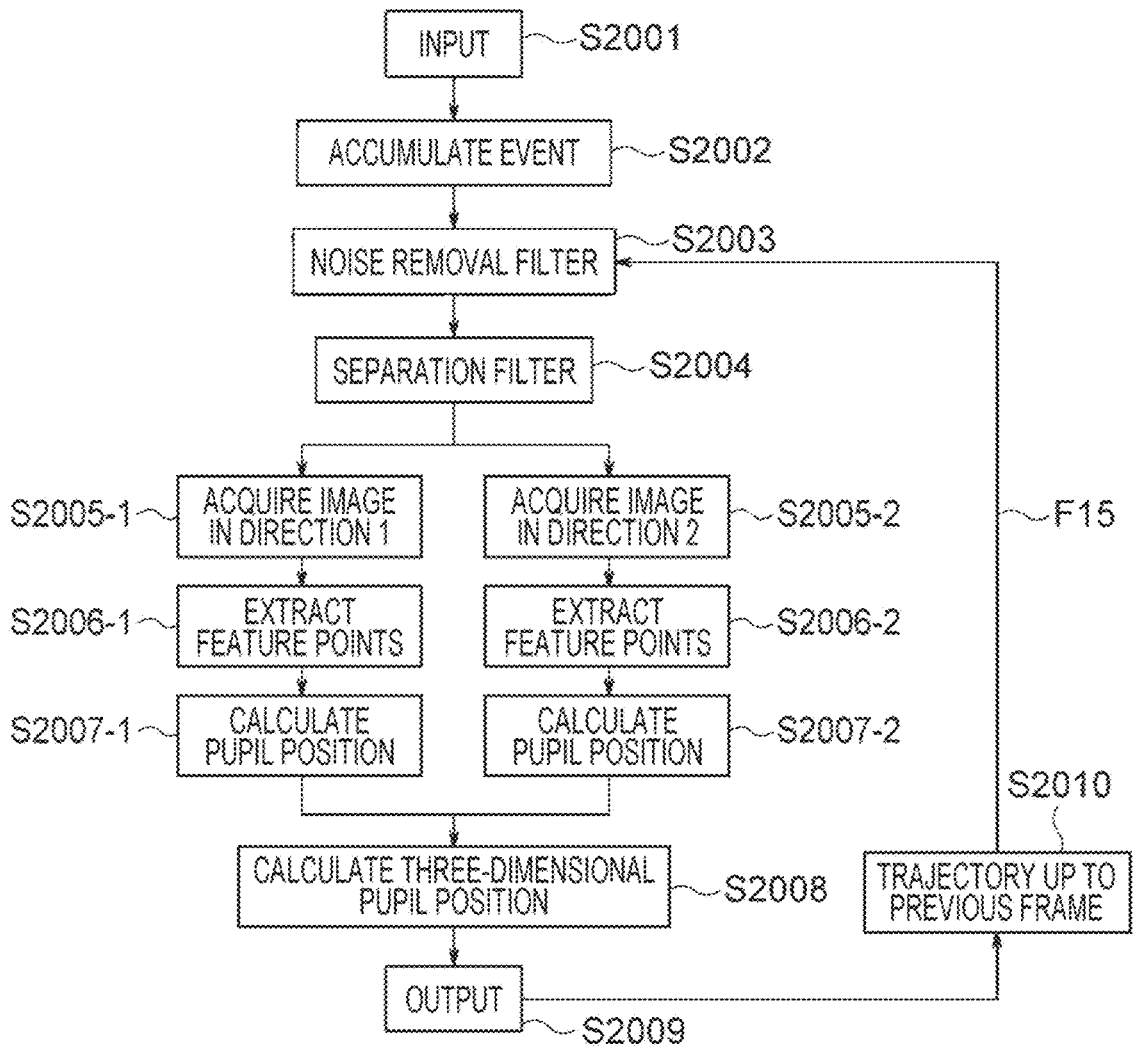
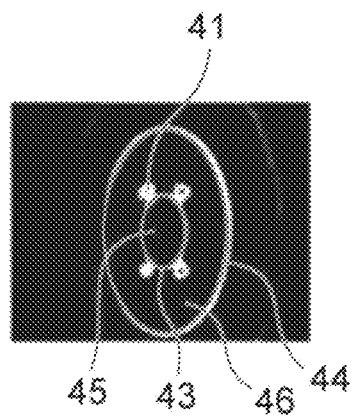
FIG. 16A
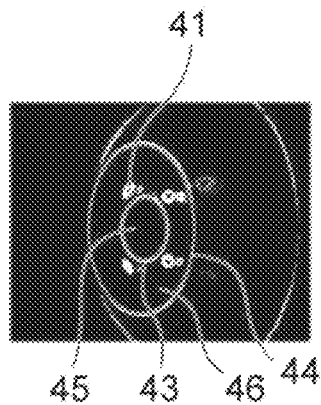
FIG. 16B

LINE-OF-SIGHT DETECTION DEVICE AND DISPLAY DEVICE

CROSS REFERENCE TO RELATED APPLICATIONS

This application is a U.S. National Phase of International Patent Application No. PCT/JP2021/032288 filed on Sep. 2, 2021, which claims priority benefit of Japanese Patent Application No. JP 2020-168764 filed in the Japan Patent Office on Oct. 5, 2020. Each of the above-referenced applications is hereby incorporated herein by reference in its entirety.

TECHNICAL FIELD

The present technology relates to a line-of-sight detection device and a display device.

BACKGROUND ART

Sensing eyeball information is expected to have a variety of development destinations. In the research field, it is expected to be used in neuroscience, bioengineering, and medicine, and in the industrial field, it is expected to be used for passing on technology, improving usability of UX through eye tracking, and the like, and furthermore, development to security through iris authentication is also expected. In recent years, head-mounted displays (AR/VR), which are increasingly being developed, have been used for foveated rendering and expansion of viewable areas (eyeboxes).

For example, in the technology proposed in Patent Document 1, by arranging a plurality of types of diffraction gratings in front of the eyes and dividing the angle of view, information regarding light of a plurality of angles can be acquired by an image sensor.

CITATION LIST

Patent Document

Patent Document 1: Japanese translation of PCT international application No. 2018-530781 (Applicant: Magic Leap)

SUMMARY OF THE INVENTION

Problems to be Solved by the Invention

However, in the technology proposed in Patent Document 1, there is a possibility that it is not possible to achieve further improvement in line-of-sight detection accuracy, achieve low latency, and achieve low power consumption.

Accordingly, the present technology has been made in view of such a situation, and a main object thereof is to provide a line-of-sight detection device and a display device including the line-of-sight detection device, which are capable of achieving further improvement in line-of-sight detection accuracy, achieving low latency, and achieving low power consumption.

Solutions to Problems

As a result of intensive research to solve the above-described object, the present inventors have surprisingly succeeded in achieving further improvement in line-of-sight detection accuracy, achieving low latency, and achieving low power consumption, and have completed the present technology.

That is, according to the present technology, as a first aspect, a line-of-sight detection device including:
- an imaging element;
- an illumination unit that illuminates an eyeball with a plurality of beams of illumination light;
- an optical element that guides respective beams of reflected light in a plurality of directions from the eyeball caused by the plurality of beams of illumination light to a direction of the imaging element;
- an optical system that causes the imaging element to non-selectively receive the beams of reflected light in the plurality of directions from the eyeball; and
- a calculation unit that converts, on the basis of the beams of reflected light in the plurality of directions from the eyeball received by the imaging element, the beams of reflected light into information of eyeball movement and/or positional information of a pupil.

In the line-of-sight detection device of the first aspect according to the present technology, the imaging element may have an event-driven function.

In the line-of-sight detection device of the first aspect according to the present technology, the optical system may cause the imaging element to receive the beams of reflected light in the plurality of directions from the eyeball without spatial assignment.

In the line-of-sight detection device of the first aspect according to the present technology,
- the optical element may include a plurality of optical elements, and
- each of the plurality of optical elements may guide respective beams of reflected light in the plurality of directions from the eyeball to the direction of the imaging element.

In the line-of-sight detection device of the first aspect according to the present technology,
- the optical element may include a plurality of optical elements, and
- at least one optical element of the plurality of optical elements may be a diffraction grating.

In the line-of-sight detection device of the first aspect according to the present technology,
- a beam of reflected light in one of the plurality of directions from the eyeball may be a beam of light from an optical axis of the eyeball.

In the line-of-sight detection device of the first aspect according to the present technology,
- the optical element may include a plurality of optical elements,
- the plurality of optical elements may include a first optical element and a second optical element, and
- a difference between reflectance of the first optical element and reflectance of the second optical element may be 50% or more.

In the line-of-sight detection device of the first aspect according to the present technology,
- the optical element may include a plurality of optical elements,
- the plurality of optical elements may include a first optical element and a second optical element, and
- a difference between diffraction efficiency of the first optical element and diffraction efficiency of the second optical element may be 50% or more.

In the line-of-sight detection device of the first aspect according to the present technology, an amount of light reaching the imaging element of a beam of reflected light from an optical axis of the eyeball among the beams of reflected light in the plurality of directions from the eyeball, may be larger than an amount of light reaching the imaging element of a beam of reflected light other than the beam of reflected light from the optical axis of the eyeball among the beams of reflected light in the plurality of directions from the eyeball.

The line-of-sight detection device of the first aspect according to the present technology may include at least one of a polarizing plate, an ND filter, or a retardation film, and in this case, by using at least one of the polarizing plate, the ND filter, or the retardation film, an amount of light reaching the imaging element of a beam of reflected light in at least one direction among the beams of reflected light in the plurality of directions from the eyeball may be adjusted.

In the line-of-sight detection device of the first aspect according to the present technology, the calculation unit may separate information of the beams of reflected light in the plurality of directions from the eyeball received by the imaging element into information of beams of reflected light in respective directions of the plurality of directions from the eyeball received by the imaging element, and convert, on the basis of each of separated pieces of the information, the each of separated pieces of the information into the information of the eyeball movement and/or the positional information of the pupil.

In the line-of-sight detection device of the first aspect according to the present technology, the optical element may generate a difference in an amount of light reaching the imaging element of beams of reflected light in at least two directions among the beams of reflected light in the plurality of directions from the eyeball, and the calculation unit may separate information of the beams of reflected light in the at least two directions received by the imaging element into information of beams of reflected light in respective directions of the at least two directions according to the difference in the amount of light, and convert, on the basis of at least two separated pieces of the information, the at least two separated pieces of the information into the information of the eyeball movement and/or the positional information of the pupil.

In the line-of-sight detection device of the first aspect according to the present technology, the optical element may generate a difference in aberration of beams of reflected light in at least two directions among the beams of reflected light in the plurality of directions from the eyeball, the calculation unit may include a low-pass filter and a high-pass filter and perform Fourier transform on information of beams of reflected light in at least two directions received by the imaging element, separate the information of the beams of reflected light in the at least two directions into information of beams of reflected light in respective directions of the at least two directions according to the difference in the aberration using the low-pass filter and the high-pass filter, and convert, on the basis of at least two separated pieces of the information, the at least two separated pieces of the information into the information of the eyeball movement and/or the positional information of the pupil.

In the line-of-sight detection device of the first aspect according to the present technology, the calculation unit may acquire a point group in a time direction by using each of pieces of information of beams of reflected light in at least two directions among pieces of information of the beams of reflected light in the plurality of directions from the eyeball received by the imaging element, and generate at least two optical flows, separate the information of the beams of reflected light in the at least two directions into information of beams of reflected light in respective directions of the at least two directions according to a difference between the at least two optical flows, and convert, on the basis of at least two separated pieces of the information, the at least two separated pieces of the information into the information of the eyeball movement and/or the positional information of the pupil.

In the line-of-sight detection device of the first aspect according to the present technology, the calculation unit may separate information of the beams of reflected light in the plurality of directions from the eyeball received by the imaging element into information of beams of reflected light in respective directions of the plurality of directions from the eyeball received by the imaging element by using a deep neural network, and convert, on the basis of each of separated pieces of the information, the each of separated pieces of the information into the information of the eyeball movement and/or the positional information of the pupil.

In the line-of-sight detection device of the first aspect according to the present technology, the imaging element may be a CMOS image sensor.

In the line-of-sight detection device of the first aspect according to the present technology, the calculation unit may include a high-pass filter, convert information of the beams of reflected light in the plurality of directions from the eyeball received by the CMOS image sensor into edge information by using the high-pass filter, separate the information of the beams of reflected light in the plurality of directions from the eyeball received by the CMOS image sensor into information of beams of reflected light in respective directions of the plurality of directions from the eyeball received by the CMOS image sensor by using the edge information, and convert, on the basis of each of separated pieces of the information, the each of separated pieces of the information into the information of the eyeball movement and/or the positional information of the pupil.

According to a second aspect according to the present technology, a display device including at least the line-of-sight detection device of the first aspect according to the present technology may be provided.

According to the present technology, further improvement of line-of-sight detection accuracy, low latency, and low power consumption can be achieved. Note that the effects described here are not necessarily limited, and may be any effect described in the present disclosure.

BRIEF DESCRIPTION OF DRAWINGS

FIG. 1 is a diagram illustrating a configuration example of a line-of-sight detection device of a first embodiment to which the present technology is applied.

FIGS. 2A, 2B, and 2C are diagrams illustrating an image when sensing of an eyeball is performed using a camera such as a CMOS image sensor.

FIGS. 3A, 3B, 3C, and 3D are diagrams illustrating an image when sensing of the eyeball is performed using the line-of-sight detection device of the first embodiment to which the present technology is applied.

FIG. 5 is a diagram illustrating a configuration example of a line-of-sight detection device of a second embodiment to which the present technology is applied.

FIGS. 6A, 6B, and 6C are diagrams schematically illustrating an image when sensing of the eyeball is performed using the line-of-sight detection device of the second embodiment to which the present technology is applied.

FIG. 7 is a diagram illustrating a configuration example of a line-of-sight detection device of a third embodiment to which the present technology is applied.

FIGS. 8A, 8B, and 8C are diagrams schematically illustrating an image when sensing of the eyeball is performed using the line-of-sight detection device of the third embodiment to which the present technology is applied.

FIG. 9 is a diagram illustrating a configuration example of a line-of-sight detection device of a fourth embodiment to which the present technology is applied.

FIGS. 10A, 10B, and 10C are diagrams illustrating an image when sensing of the eyeball is performed using the line-of-sight detection device of the fourth embodiment to which the present technology is applied.

FIGS. 11A, 11B, 11C, and 11D are diagrams schematically illustrating an image when edge detection is performed on the image illustrated in FIGS. 10A, 10B, and 10C.

FIG. 15 is a diagram illustrating an example of a flow up to calculation of the three-dimensional eye (pupil) position using the line-of-sight detection device of the fifth embodiment to which the present technology is applied.

FIGS. 16A and 16B are diagrams schematically illustrating an image when sensing of the eyeball is performed using a line-of-sight detection device of a sixth embodiment to which the present technology is applied.

MODE FOR CARRYING OUT THE INVENTION

Figure 4:
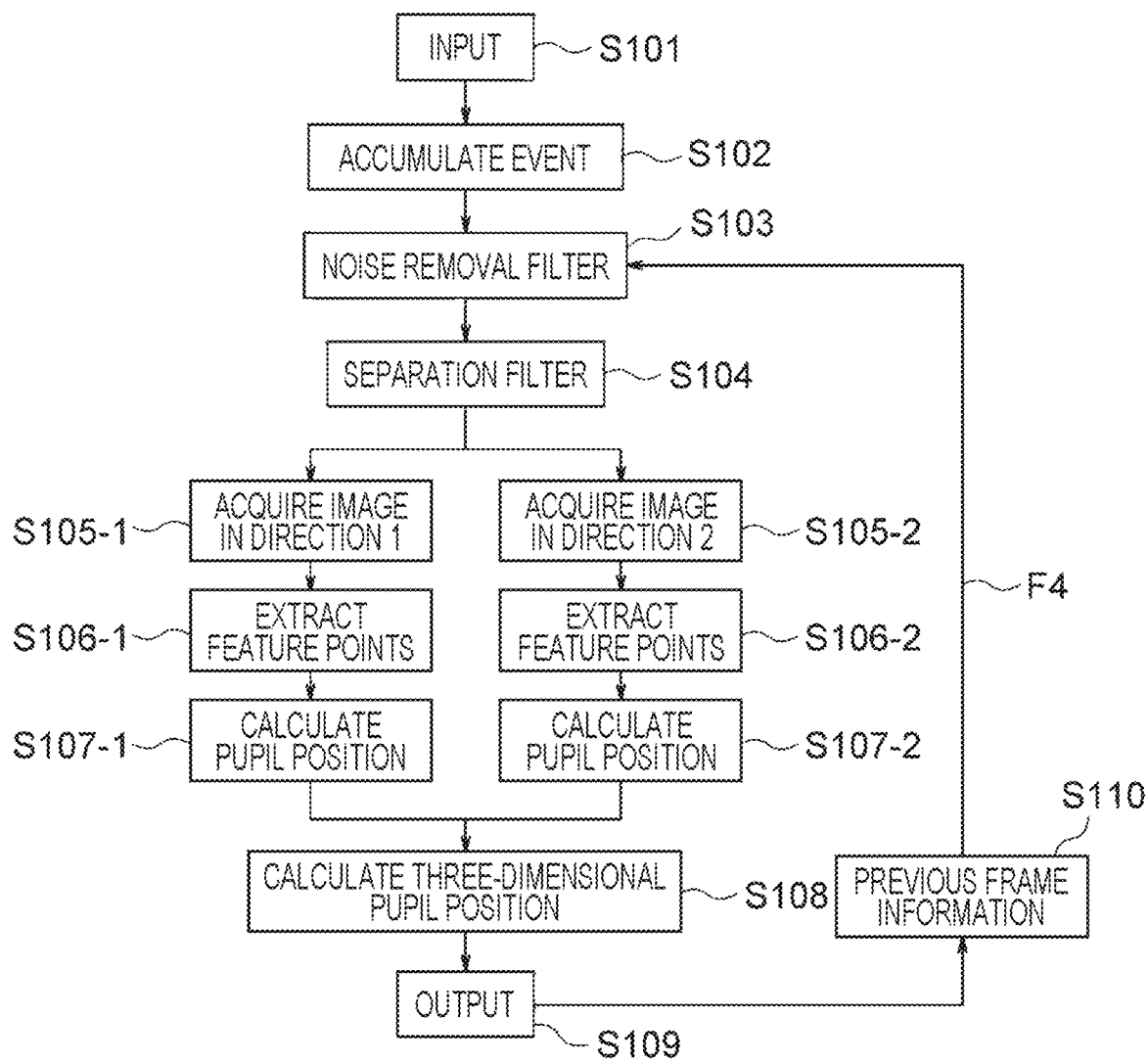
FIG. 4 is a diagram illustrating an example of a flow up to calculation of a three-dimensional eye (pupil) position using the line-of-sight detection device of the first embodiment to which the present technology is applied.

Hereinafter, preferred embodiments for carrying out the present technology will be described. Note that the embodiments described below are examples of representative embodiments of the present technology, and the scope of the present technology is not interpreted in a narrow sense by them. Note that unless otherwise specified, in the drawings, "upper" means an upper direction or an upper side in the drawings, "lower" means a lower direction or a lower side in the drawings, "left" means a left direction or a left side in the drawings, and "right" means a right direction or a right side in the drawings. Furthermore, in the description using the drawings, the same or equivalent elements or members are designated by the same reference numerals, and duplicate descriptions will be omitted.

Note that the description will be made in the following order.
1. Overview of present technology
2. First embodiment (Example 1 of line-of-sight detection device)
3. Second embodiment (Example 2 of line-of-sight detection device)
4. Third Embodiment (Example 3 of line-of-sight detection device)
5. Fourth embodiment (Example 4 of line-of-sight detection device)
6. Fifth embodiment (Example 5 of line-of-sight detection device)
7. Sixth embodiment (Example 6 of line-of-sight detection device)
8. Seventh embodiment (Example 7 of line-of-sight detection device)
9. Eighth Embodiment (Example 1 of display device)

1. Overview of Present Technology

First, the overview of the present technology will be described. The present technology relates to a line-of-sight detection device and a display device.

In order to receive light beams from two directions, there is a technology of spatially dividing the inside of a light receiving element (imaging element) as Technology Example 1. In Technology Example 1, by arranging a plurality of types of diffraction gratings in front of the eyes and dividing the angle of view, information regarding light of a plurality of angles can be acquired by an image sensor. It is possible to use information of a good angle according to the angle of the eyeball.

Furthermore, as Technical Example 2, there is a technology of time division by a light receiving element (imaging element), and as Technical Example 3, there is a technology of using a plurality of light receiving elements (imaging elements).

Incidentally, it is also conceivable to receive information of light from different directions by one imaging element, but in this case, semantic segmentation using a Deep Neural Network is generally performed. There are many cases where the accuracy of separating two translucent bodies is not achieved or is not satisfactory, and there are many cases where a more complicated layer structure is required and the power consumption is further increased.

The present technology has been made in view of such a situation. In the present technology, information of light from a plurality of directions (for example, two directions) is non-selectively (for example, without spatial (pixel) assignment) received by an imaging element in the same space (pixel), and pixel separation or an eye (pupil) position as it is can be detected in a subsequent process. Therefore, in a case of a dynamic vision sensor (DVS) in which there is no deterioration in resolution and only minimum edge information in particular is acquired, even if information of light from a plurality of directions (for example, two directions) is acquired, detection processing can be performed without increasing the data amount. Furthermore, depth estimation is also possible by calculating the eye (pupil) center in each direction and the amount of deviation thereof.

Hereinafter, preferred embodiments for carrying out the present technology will be described in detail with reference to the drawings. Note that the embodiments described below are examples of representative embodiments of the present technology, and the scope of the present technology is not interpreted in a narrow sense by them.

2. First Embodiment (Example 1 of Line-of-Sight Detection Device)

A line-of-sight detection device of a first embodiment (Example 1 of the line-of-sight detection device) according to the present technology is a line-of-sight detection device including an imaging element, an illumination unit that illuminates an eyeball with a plurality of beams of illumination light, an optical element that guides respective beams of reflected light in a plurality of directions from the eyeball caused by the plurality of beams of illumination light to a direction of the imaging element, an optical system that causes the imaging element to non-selectively receive the beams of reflected light in the plurality of directions from the eyeball, and a calculation unit that converts, on the basis of the beams of reflected light in the plurality of directions from the eyeball received by the imaging element, the beams of reflected light into information of eyeball movement and/or positional information of a pupil. The imaging element included in the line-of-sight detection device of the first embodiment according to the present technology may be an imaging element (for example, DVS (Dynamic Vision Sensor)) having an event-driven function.

Hereinafter, the line-of-sight detection device of the first embodiment (Example 1 of the line-of-sight detection device) according to the present technology will be described with reference to FIGS. 1, 2A, 2B, 20, 3A, 3B, 3C, 3D, and 4.

First, a line-of-sight detection device 1001 will be described with reference to FIG. 1.

The line-of-sight detection device 1001 illustrated in FIG. 1 includes a dynamic vision sensor (DVS) 1, an LED (illumination unit) 7 that illuminates an eyeball with a plurality of (for example, two) beams of illumination light, a first optical element 51 and a second optical element 61 that guide a first beam of reflected light L1-1 (beam of light from an optical axis of the eyeball 500) and a second beam of reflected light L1-2 from the eyeball 500 caused by the plurality of (for example, two) beams of illumination light to a direction of the dynamic vision sensor (DVS) 1, an optical system (not illustrated) that causes the dynamic vision sensor (DVS) 1 to non-selectively receive the first beam of reflected light L1-1 and the second beam of reflected light L1-2 in the two directions from the eyeball 500, and a calculation unit (not illustrated) that converts, on the basis of the first beam of reflected light L1-1 and the second beam of reflected light L1-2 in the two directions from the eyeball received by the dynamic vision sensor (DVS) 1, the beams of reflected light into information of the eyeball 500 movement and/or positional information of the pupil. The optical system can cause the dynamic vision sensor (DVS) 1 to non-selectively receive the first beam of reflected light L1-1 and the second beam of reflected light L1-2 in two directions from the eyeball 500 without spatial assignment.

The first optical element 51 is a holographic optical element (HOE) grating (hologram diffraction grating), and the second optical element 61 is a holographic optical element (HOE) mirror (hologram mirror). Note that the first optical element 51 may be the HOE (holographic optical element) mirror (hologram mirror), the second optical element 61 may be the HOE (holographic optical element) mirror (hologram mirror), and the first optical element 51 and/or the first optical element 61 may be a mirror (for example, a half mirror).

The first optical element 51 and the second optical element 61 are disposed on the substrate 4. The substrate 4 may be a transparent substrate or an impermeable substrate. The substrate 4 is, for example, a light guide plate, a glass plate, or the like.

In the line-of-sight detection device 1001, the beams of reflected light in two directions (the first beam of reflected light L1-1 and the second beam of reflected light L1-2) from the eyeball 500 has been described, but the line-of-sight detection device 1001 can also be applied to the beams of reflected light in three or more directions from the eyeball 500.

FIGS. 2A, 2B, and 2C are diagrams illustrating an image when sensing of an eyeball is performed using a camera such as a CMOS image sensor instead of the dynamic vision sensor (DVS) 1, and more specifically, FIG. 2A is a diagram illustrating an image of the camera such as a CMOS image sensor based on information of the first beam of reflected light L1-1 (first beam of deflected light L1-1a) from the eyeball 500, FIG. 2B is a diagram illustrating an image of the camera such as a CMOS image sensor based on information of the second beam of reflected light L1-2 (second beam of deflected light L1-2a) from the eyeball 500, FIG. 2C is a diagram illustrating an image of the camera such as a CMOS image sensor based on the first beam of reflected light L1-1 (first beam of deflected light L1-1a) and the second beam of reflected light L1-2 (second beam of deflected light L1-2a) when the camera such as a CMOS image sensor simultaneously receives the first beam of reflected light L1-1 (first beam of deflected light L1-1a) and the second beam of reflected light L1-2 (second beam of deflected light L1-2a) from the eyeball 500. In FIGS. 2A, 2B, and 2C, a Purkinje image 41, a pupil 45, an iris 46, a sclera 47, a boundary portion (edge portion) 43 between the pupil 45 and the iris 46, and a boundary portion (edge portion) 44 between the iris 46 and the sclera 47 are illustrated.

FIGS. 3A, 3B, 3C, and 3D are diagrams illustrating an image when sensing of the eyeball is performed using the line-of-sight detection device (line-of-sight detection device 1001) of the first embodiment according to the present technology, and more specifically, FIG. 3A is a diagram illustrating an image of the dynamic vision sensor (DVS) 1 based on the first beam of reflected light L1-1 (first beam of deflected light L1-1a) and the second beam of reflected light L1-2 (second beam of deflected light L1-2a) when the dynamic vision sensor (DVS) 1 simultaneously receives the first beam of reflected light L1-1 (first beam of deflected light L1-1a) and the second beam of reflected light L1-2 (second beam of deflected light L1-2a) from the eyeball 500. FIG. 3B is an image of the dynamic vision sensor (DVS) 1 based on information of the first beam of reflected light L1-1 (first beam of deflected light L1-1a) separated from the image of the dynamic vision sensor (DVS) 1 illustrated in FIG. 3A, and FIG. 3C is an image of the dynamic vision sensor (DVS) 1 based on information of the second beam of reflected light L1-2 (first beam of deflected light L1-2a) separated from the image of the dynamic vision sensor (DVS) 1 illustrated in FIG. 3A. Then, FIG. 3D is an image obtained by combining the separated image of the dynamic vision sensor (DVS) 1 illustrated in FIG. 3B and the separated image of the dynamic vision sensor (DVS) 1 illustrated in FIG. 3C.

In FIGS. 3A, 3B, 3C, and 3D, the Purkinje image 41, a central portion 42 of the pupil, the pupil 45, the iris 46, the sclera 47, the boundary portion (edge portion) 43 between the pupil 45 and the iris 46, and the boundary portion (edge portion) 44 between the iris 46 and the sclera 47 are illustrated. As illustrated in FIGS. 3A, 3B, and 3C, the image of the dynamic vision sensor (DVS) 1 includes only edge information (in FIGS. 3A, 3B, 3C, and 3D, it is a white portion, and note that the central portion 42 of the pupil is white for the sake of convenience) such as the Purkinje image 41, the boundary portion (edge portion) 43 between the pupil 45 and the iris 46, and the boundary portion (edge portion) 44 between the iris 46 and the sclera 47, so that image separation is easy. When the dynamic vision sensor (DVS) 1 is used, the amount of image information can be reduced in processing such as image separation.

FIG. 4 is a diagram illustrating an example of a flow up to calculation of a three-dimensional eye (pupil) position using the line-of-sight detection device of the first embodiment according to the present technology.

In step S101 illustrated in FIG. 4, for example, image (video) information (image (video) information based on beams of reflected light in two directions (three or more directions may be used) from the eyeball simultaneously received by DVS) from a beam of reflected light from the optical axis of the eyeball and a beam of reflected light from the eyeball other than the beam of reflected light from the optical axis of the eyeball (for example, in two directions, but three or more directions may be used) is input.

In step S102, the event information generated in a predetermined fixed period is accumulated.

In step S103, noise removal is performed using a noise removal filter.

In step S104, the calculation unit included in the line-of-sight detection device of the first embodiment according to the present technology separates, for example, the image (video) information from the beam of reflected light from the optical axis of the eyeball and the image (video) information from the beam of reflected light from the eyeball other than the beam of reflected light from the optical axis of the eyeball using the separation filter.

In step S105-1, the separated image (video) information in direction 1 (for example, the beam of reflected light from the optical axis of the eyeball) is acquired.

In step S106-1, feature points are extracted from the image (video) information in direction 1 (for example, the beam of reflected light from the optical axis of the eyeball).

In step S107-1, for example, the eye (pupil) position is calculated by elliptical fitting using the image (video) information in direction 1 (for example, the beam of reflected light from the optical axis of the eyeball).

In step S105-2, the separated image (video) information in direction 2 (for example, the beam of reflected light from the eyeball other than the beam of reflected light from the optical axis of the eyeball) is acquired.

In step S106-2, feature points are extracted from image (video) information in direction 2 (for example, the beam of reflected light from the eyeball other than the beam of reflected light from the optical axis of the eyeball).

In step S107-2, for example, the eye (pupil) position is calculated by elliptical fitting using the image (video) information in direction 2 (for example, the beam of reflected light from the eyeball other than the beam of reflected light from the optical axis of the eyeball).

In step S108, coordinates of a three-dimensional eye (pupil) position are calculated from the amount of deviation between the eye (pupil) position obtained in step S107-1 and the eye (pupil) position obtained in step S107-2, and three-dimensional eye (pupil) positional information is output in step S109.

In a case where it is desired to use information regarding a region of interest (ROI), separation auxiliary data (data obtained when the images are separated in step S104, and the like), data regarding the feature point extraction in steps S106-1 and S106-2, and the like, which have been output in step S109, for the next frame as previous frame information, the processing proceeds to step S110. In step S110, as the previous frame information, the information regarding the region of interest (ROI), the separation auxiliary data (data obtained when the images are separated in step S104, and the like), the data regarding the feature point extraction in steps S106-1 and 106-2, and the like are fed back to step S103 (noise removal using the noise removal filter) (arrow F4).

As described above, the content described for the line-of-sight detection device of the first embodiment (Example 1 of the line-of-sight detection device) according to the present technology can be applied to the line-of-sight detection devices of the second to seventh embodiments according to the present technology as described later unless there is a particular technical contradiction.

3. Second Embodiment (Example 2 of Line-of-Sight Detection Device)

A line-of-sight detection device of a second embodiment (Example 1 of the line-of-sight detection device) according to the present technology is a line-of-sight detection device including an imaging element, an illumination unit that illuminates an eyeball with a plurality of beams of illumination light, an optical element that guides respective beams of reflected light in a plurality of directions from the eyeball caused by the plurality of beams of illumination light to a direction of the imaging element, an optical system that causes the imaging element to non-selectively receive the beams of reflected light in the plurality of directions from the eyeball, and a calculation unit that converts, on the basis of the beams of reflected light in the plurality of directions from the eyeball received by the imaging element, the beams of reflected light into information of eyeball movement and/or positional information of a pupil. The imaging element included in the line-of-sight detection device of the second embodiment according to the present technology may be an imaging element (for example, DVS (Dynamic Vision Sensor)) having an event-driven function.

In the line-of-sight detection device of the second embodiment according to the present technology, the optical element includes a plurality of optical elements, the plurality of optical elements includes a first optical element and a second optical element, and a difference between reflectance of the first optical element and reflectance of the second optical element is 50% or more, or a difference between diffraction efficiency of the first optical element and diffraction efficiency of the second optical element is 50% or more.

In the line-of-sight detection device of the second embodiment according to the present technology, the amount of light reaching the imaging element of a beam of reflected light from an optical axis of the eyeball among the beams of reflected light in the plurality of directions from the eyeball may be larger than the amount of light reaching the imaging element of a beam of reflected light other than the beam of reflected light from the optical axis of the eyeball among the beams of reflected light in the plurality of directions from the eyeball.

Hereinafter, the line-of-sight detection device of the second embodiment (Example 2 of the line-of-sight detection device) according to the present technology will be described with reference to FIGS. 5, 6A, 6B, [to] and 6C.

First, a line-of-sight detection device 1005 will be described with reference to FIG. 5.

The line-of-sight detection device 1005 illustrated in FIG. 5 includes a dynamic vision sensor (DVS) 1, an LED (illumination unit) 7 that illuminates an eyeball with a plurality of (for example, two) beams of illumination light, a first optical element 55 and a second optical element 66 that guide a first beam of reflected light L5-1 (beam of light from the optical axis of the eyeball 500) and a second beam of reflected light L5-2 from the eyeball 500 caused by the plurality of (for example, two) beams of illumination light to a direction of the dynamic vision sensor (DVS) 1, an optical system (not illustrated) that causes the dynamic vision sensor (DVS) 1 to non-selectively receive the first beam of reflected light L5-1 and the second beam of reflected light L5-2 in the two directions from the eyeball 500, and a calculation unit (not illustrated) that converts, on the basis of the first beam of reflected light L5-1 and the second beam of reflected light L5-2 in the two directions from the eyeball received by the dynamic vision sensor (DVS) 1, the beams of reflected light into information of movement of the eyeball 500 and/or positional information of the pupil. The optical system can cause the dynamic vision sensor (DVS) 1 to non-selectively receive the first beam of reflected light L5-1 and the second beam of reflected light L5-2 in two directions from the eyeball 500 without spatial assignment.

The first optical element 55 is the HOE (holographic optical element) grating (hologram diffraction grating), and the second optical element 65 is the HOE (holographic optical element) mirror (hologram mirror). Note that the first optical element 55 may be the HOE (holographic optical element) mirror (hologram mirror), the second optical element 65 may be the HOE (holographic optical element) mirror (hologram mirror), and the first optical element 55 and/or the first optical element 65 may be a mirror (for example, a half mirror).

The first optical element 55 and the second optical element 65 are disposed on the substrate 4. The substrate 4 may be a transparent substrate or an impermeable substrate. The substrate 4 is, for example, a light guide plate, a glass plate, or the like.

In the line-of-sight detection device 1005, the beams of reflected light in two directions (the first beam of reflected light L5-1 and the second beam of reflected light L5-2) from the eyeball 500 has been described, but the line-of-sight detection device 1005 can also be applied to the beams of reflected light in three or more directions from the eyeball 500.

FIGS. 6A, 6B, and 6C are diagrams illustrating an image when sensing of the eyeball is performed using the line-of-sight detection device (line-of-sight detection device 1005) of the second embodiment according to the present technology, and more specifically, FIG. 6C is a diagram illustrating an image of the dynamic vision sensor (DVS) 1 based on the first beam of reflected light L5-1 (first beam of deflected light L5-1a) and the second beam of reflected light L5-2 (second beam of deflected light L5-2a) when the dynamic vision sensor (DVS) 1 simultaneously receives the first beam of reflected light L5-1 (first beam of deflected light L5-1a) and the second beam of reflected light L5-2 (second beam of deflected light L5-2a) from the eyeball 500. FIG. 6A is an image of the dynamic vision sensor (DVS) 1 based on information of the first beam of reflected light L5-1 (first beam of deflected light L5-1a) obtained by image-separating the image of the dynamic vision sensor (DVS) 1 illustrated in FIG. 6C, and FIG. 6B is an image of the dynamic vision sensor (DVS) 1 based on information of the second beam of reflected light L1-2 (first beam of deflected light L1-2a) obtained by image-separating the image of the dynamic vision sensor (DVS) 1 illustrated in FIG. 6C.

The diffraction efficiency of the first optical element 55 is higher than the diffraction efficiency of the second optical element 65, and thus the amount of light reaching the dynamic vision sensor (DVS) 1 of a beam of deflected light L5-1a is larger than the amount of light reaching the dynamic vision sensor (DVS) 1 of a beam of deflected light L5-2a. Therefore, the edge portion (the boundary portion (edge portion) 43 between the pupil 45 and the iris 46 and the boundary portion (edge portion) 44 between the iris 46 and the sclera 47) of the image of the dynamic vision sensor (DVS) 1 illustrated in FIG. 6A is clearly viewed in white and more vividly on FIGS. 6A and 6B (on the paper surface) than the edge portion (the boundary portion (edge portion) 43 between the pupil 45 and the iris 46 and the boundary portion (edge portion) 44 between the iris 46 and the sclera 47) of the image of the dynamic vision sensor (DVS) 1 illustrated in FIG. 6B. That is, the edge portion (the boundary portion (edge portion) 43 between the pupil 45 and the iris 46 and the boundary portion (edge portion) 44 between the iris 46 and the sclera 47) of the image of the dynamic vision sensor (DVS) 1 illustrated in FIG. 6A has a larger event occurrence amount and higher sensitivity and luminance than the edge portion (the boundary portion (edge portion) 43 between the pupil 45 and the iris 46 and the boundary portion (edge portion) 44 between the iris 46 and the sclera 47) of the image of the dynamic vision sensor (DVS) 1 illustrated in FIG. 6B.

As described above, the content described for the line-of-sight detection device of the second embodiment (Example 2 of the line-of-sight detection device) according to the present technology can be applied to the line-of-sight detection device of the first embodiment according to the present technology described above and line-of-sight detection devices of the third to seventh embodiments according to the present technology as described later unless there is a particular technical contradiction.

4. Third Embodiment (Example 3 of Line-of-Sight Detection Device)

A line-of-sight detection device of a third embodiment (Example 3 of the line-of-sight detection device) according to the present technology is a line-of-sight detection device including an imaging element, an illumination unit that illuminates an eyeball with a plurality of beams of illumination light, an optical element that guides respective beams of reflected light in a plurality of directions from the eyeball caused by the plurality of beams of illumination light to a direction of the imaging element, an optical system that causes the imaging element to non-selectively receive the beams of reflected light in the plurality of directions from the eyeball, and a calculation unit that converts, on the basis of the beams of reflected light in the plurality of directions from the eyeball received by the imaging element, the beams of reflected light into information of eyeball movement and/or positional information of a pupil, in which at least one of a polarizing plate, an ND filter, or a retardation film is further provided. The imaging element included in the line-of-sight detection device of the third embodiment according to the present technology may be an imaging element (for example, DVS (Dynamic Vision Sensor)) having an event-driven function.

In the line-of-sight detection device of the third embodiment according to the present technology, by using at least one of the polarizing plate, the ND filter, or the retardation film, the amount of light reaching the imaging element of a beam of reflected light in at least one direction among the beams of reflected light in the plurality of directions from the eyeball can be adjusted.

Hereinafter, the line-of-sight detection device of the third embodiment (Example 3 of the line-of-sight detection device) according to the present technology will be described with reference to FIGS. 7, 8A, 8B, and 8C.

First, a line-of-sight detection device 1007 will be described with reference to FIG. 7.

The line-of-sight detection device 1007 illustrated in FIG. 7 includes a dynamic vision sensor (DVS) 1, an LED (illumination unit) 7 that illuminates an eyeball with a plurality of (for example, two) beams of illumination light, a first optical element 57 and a second optical element 67 that guide a first beam of reflected light L7-1 (first polarized light) (beam of light from the optical axis of the eyeball 500) and a second beam of reflected light L7-2 (second polarized light) from the eyeball 500 caused by the plurality of (for example, two) beams of illumination light to a direction of the dynamic vision sensor (DVS) 1, an optical system (not illustrated) that causes the dynamic vision sensor (DVS) 1 to non-selectively receive the first beam of reflected light L7-1 and the second beam of reflected light L7-2 in two directions from the eyeball 500, and a calculation unit (not illustrated) that converts, on the basis of the first beam of reflected light L7-1 and the second beam of reflected light L7-2 in the two directions from the eyeball received by the dynamic vision sensor (DVS) 1, the beams of reflected light into information of movement of the eyeball 500 and/or positional information of the pupil. Furthermore, the line-of-sight detection device 1007 includes a polarizing plate 87-1 disposed above the LED (illumination unit) 7 (lower right side in FIG. 7), a retardation film 97 disposed above the second optical element 67 (lower side in FIG. 7), and a polarizing plate 87-2 disposed above the dynamic vision sensor (DVS) 1 (upper left side in FIG. 7). Note that the retardation film 97 may be disposed on the first optical element 57 (lower side in FIG. 7) instead of being disposed on the second optical element 67 (lower side in FIG. 7). The optical system can cause the dynamic vision sensor (DVS) 1 to non-selectively receive the first beam of reflected light L7-1 and the second beam of reflected light L7-2 in two directions from the eyeball 500 without spatial assignment.

The first optical element 57 is the HOE (holographic optical element) grating (hologram diffraction grating), and the second optical element 67 is the HOE (holographic optical element) mirror (hologram mirror). Note that the first optical element 57 may be the HOE (holographic optical element) mirror (hologram mirror), the second optical element 67 may be the HOE (holographic optical element) mirror (hologram mirror), and the first optical element 57 and/or the first optical element 67 may be a mirror (for example, a half mirror).

The first optical element 57 and the second optical element 67 are disposed on the substrate 4. The substrate 4 may be a transparent substrate or an impermeable substrate. The substrate 4 is, for example, a light guide plate, a glass plate, or the like.

In the line-of-sight detection device 1007, the beams of reflected light in two directions (the first beam of reflected light L5-1 and the second beam of reflected light L5-2) from the eyeball 500 has been described, but the line-of-sight detection device 1007 can also be applied to the beams of reflected light in three or more directions from the eyeball 500.

FIGS. 8A, 8B, and 8C are diagrams illustrating an image when sensing of the eyeball is performed using the line-of-sight detection device (line-of-sight detection device 1007) of the third embodiment according to the present technology, and more specifically, FIG. 8C is a diagram illustrating an image of the dynamic vision sensor (DVS) 1 based on the first beam of reflected light L7-1 (first beam of deflected light L7-1a) and the second beam of reflected light L7-2 (second beam of deflected light L7-2a) when the dynamic vision sensor (DVS) 1 simultaneously receives the first beam of reflected light L7-1 (first beam of deflected light L7-1a) and the second beam of reflected light L7-2 (second beam of deflected light L7-2a) from the eyeball 500. FIG. 8A is an image of the dynamic vision sensor (DVS) 1 based on information of the first beam of reflected light L5-1 (first beam of deflected light L5-1a) obtained by image-separating the image of the dynamic vision sensor (DVS) 1 illustrated in FIG. 8C, and FIG. 6B is an image of the dynamic vision sensor (DVS) 1 based on information of the second beam of reflected light L1-2 (first beam of deflected light L1-2a) obtained by image-separating the image of the dynamic vision sensor (DVS) 1 illustrated in FIG. 6C.

As described above, since the retardation film 97 is disposed on the second optical element 97 (on the lower side in FIG. 7), the amount of the first beam of deflected light (first polarized light) L7-1a reaching the dynamic vision sensor (DVS) 1 is larger than the amount of the second beam of deflected light (second polarized light) L7-2a reaching the dynamic vision sensor (DVS) 1. Therefore, the edge portion (the boundary portion (edge portion) 43 between the pupil 45 and the iris 46 and the boundary portion (edge portion) 44 between the iris 46 and the sclera 47) of the image of the dynamic vision sensor (DVS) 1 illustrated in FIG. 8A is clearly viewed in white and more vividly on FIGS. 8A and 8B (on the paper surface) than the edge portion (the boundary portion (edge portion) 43 between the pupil 45 and the iris 46 and the boundary portion (edge portion) 44 between the iris 46 and the sclera 47) of the image of the dynamic vision sensor (DVS) 1 illustrated in FIG. 8B. That is, the edge portion (the boundary portion (edge portion) 43 between the pupil 45 and the iris 46 and the boundary portion (edge portion) 44 between the iris 46 and the sclera 47) of the image of the dynamic vision sensor (DVS) 1 illustrated in FIG. 8A has a larger event occurrence amount and higher sensitivity and luminance than the edge portion (the boundary portion (edge portion) 43 between the pupil 45 and the iris 46 and the boundary portion (edge portion) 44 between the iris 46 and the sclera 47) of the image of the dynamic vision sensor (DVS) 1 illustrated in FIG. 8B.

In the line-of-sight detection device of the third embodiment according to the present technology, it is possible to reduce Purkinje images in which polarization is preserved. In the line-of-sight detection device 1007, it is possible to reduce Purkinje images with respect to light of both the first beam of deflected light (first polarized light) L7-1a and the second beam of deflected light (second polarized light) L7-2a reaching the dynamic vision sensor (DVS) 1.

As described above, the content described for the line-of-sight detection device of the third embodiment (Example 3 of the line-of-sight detection device) according to the present technology can be applied to the line-of-sight detection devices of the first and second embodiments according to the present technology described above and the line-of-sight detection devices of the fourth to seventh embodiments according to the present technology as described later unless there is a particular technical contradiction.

5. Fourth Embodiment (Example 4 of Line-of-Sight Detection Device)

A line-of-sight detection device of a fourth embodiment (Example 4 of the line-of-sight detection device) according to the present technology is a line-of-sight detection device including an imaging element, an illumination unit that illuminates an eyeball with a plurality of beams of illumination light, an optical element that guides respective beams of reflected light in a plurality of directions from the eyeball caused by the plurality of beams of illumination light to a direction of the imaging element, an optical system that causes the imaging element to non-selectively receive the beams of reflected light in the plurality of directions from the eyeball, and a calculation unit that converts, on the basis of the beams of reflected light in the plurality of directions from the eyeball received by the imaging element, the beams of reflected light into information of eyeball movement and/or positional information of a pupil. The imaging element included in the line-of-sight detection device of the fourth embodiment according to the present technology may be a CMOS image sensor.

The calculation unit included in the line-of-sight detection device of the fourth embodiment according to the present technology can include a high-pass filter. Information of the beams of reflected light in the plurality of directions from the eyeball received by the CMOS image sensor can be converted into edge information by using the high-pass filter, and information of the beams of reflected light in the plurality of directions from the eyeball received by the CMOS image sensor can be separated into information of the beams of reflected light in respective directions of the plurality of directions from the eyeball received by the CMOS image sensor by using the edge information. Then, the information can be converted into the information of the eyeball movement and/or the positional information of the pupil on the basis of each of the separated pieces of the information. Examples of the edge information include information of a boundary portion (edge portion) between the pupil and the iris, information of a boundary portion (edge portion) between the iris and the sclera, and information of a Purkinje image, and the like.

Hereinafter, the line-of-sight detection device of the fourth embodiment (Example 4 of the line-of-sight detection device) according to the present technology will be described with reference to FIGS. 9, 10A, 10B, 10C, 11A, 11B, 11C, 11D, and 12.

First, a line-of-sight detection device 1009 will be described with reference to FIG. 9.

The line-of-sight detection device 1009 includes a camera (CMOS image sensor) 11, an LED (illumination unit) 7 that illuminates the eyeball with a plurality of (for example, two) beams of illumination light, a first optical element 59 and a second optical element 69 that guide a first beam of reflected light L9-1 (beam of light from the optical axis of the eyeball 500) and a second beam of reflected light L9-2 from the eyeball 500 caused by the plurality of (for example, two) beams of illumination light to a direction of the camera (CMOS image sensor) 11, an optical system (not illustrated) that causes the camera (CMOS image sensor) 11 to non-selectively receive the first beam of reflected light L9-1 and the second beam of reflected light L9-2 in two directions from the eyeball 500, and a calculation unit (not illustrated) that converts, on the basis of the first beam of reflected light L9-1 and the second beam of reflected light L9-2 in the two directions from the eyeball received by the camera (CMOS image sensor) 11, the beams of reflected light into information of movement of the eyeball 500 and/or the positional information of the pupil. The optical system can cause the camera (CMOS image sensor) 11 to non-selectively receive the first beam of reflected light L9-1 and the second beam of reflected light L9-2 in two directions from the eyeball 500 without spatial assignment.

The first optical element 59 is the HOE (holographic optical element) grating (hologram diffraction grating), and the second optical element 69 is the HOE (holographic optical element) mirror (hologram mirror). Note that the first optical element 59 may be the HOE (holographic optical element) mirror (hologram mirror), the second optical element 69 may be the HOE (holographic optical element) mirror (hologram mirror), and the first optical element 59 and/or the first optical element 69 may be a mirror (for example, a half mirror).

The first optical element 59 and the second optical element 69 are disposed on the substrate 4. The substrate 4 may be a transparent substrate or an impermeable substrate. The substrate 4 is, for example, a light guide plate, a glass plate, or the like.

In the line-of-sight detection device 1009, the beams of reflected light in two directions (the first beam of reflected light L5-1 and the second beam of reflected light L5-2) from the eyeball 500 has been described, but the line-of-sight detection device 1009 can also be applied to the beams of reflected light in three or more directions from the eyeball 500.

FIGS. 10A, 10B, and 10C are diagrams illustrating an image when sensing of the eyeball is performed using the line-of-sight detection device (line-of-sight detection device 1009) of the fourth embodiment according to the present technology, and more specifically, FIG. 10C is a diagram illustrating an image of the camera (CMOS image sensor) 11 based on the first beam of reflected light L1-1 (first beam of deflected light L1-1a) and the second beam of reflected light L1-2 (second beam of deflected light L1-2a) when the camera (CMOS image sensor) 11 simultaneously receives the first beam of reflected light L9-1 (first beam of deflected light L9-1a) and the second beam of reflected light L9-2

(second beam of deflected light L9-2a) from the eyeball 500. FIG. 10A is a diagram illustrating an image of the camera (CMOS image sensor) 11 based on information of the first beam of reflected light L9-1 (first beam of deflected light L9-1a) from the eyeball 500, and FIG. 10B is a diagram illustrating an image of the camera (CMOS image sensor) 11 based on information of the second beam of reflected light L9-2 (second beam of deflected light L9-2a) from the eyeball 500. In FIGS. 10A, 10B, and 10C, the Purkinje image 41, the pupil 45, the iris 46, the sclera 47, the boundary portion (edge portion) 43 between the pupil 45 and the iris 46, and the boundary portion (edge portion) 44 between the iris 46 and the sclera 47 are illustrated.

FIGS. 11A, 11B, 11C, and 11D are diagrams schematically illustrating an image when edge detection is performed on the image illustrated in FIGS. 10A, 10B, and 10C, and more specifically, FIG. 11A is a diagram illustrating an image when edge detection is performed based on the first beam of reflected light L9-1 (first beam of deflected light L9-1a) and the second beam of reflected light L9-2 (second beam of deflected light L9-2a) from the eyeball 500. FIG. 11B is an image based on information of the first beam of reflected light L9-1 (first beam of deflected light L9-1a) separated from the image when edge detection is performed illustrated in FIG. 11A, and FIG. 11C is an image based on information of the first beam of reflected light L9-1 (first beam of deflected light L9-1a) separated from the image when edge detection is performed illustrated in FIG. 11A. Then, FIG. 11D is an image obtained by combining the separated image illustrated in FIG. 11B and the separated image illustrated in FIG. 11C.

Figure 12:
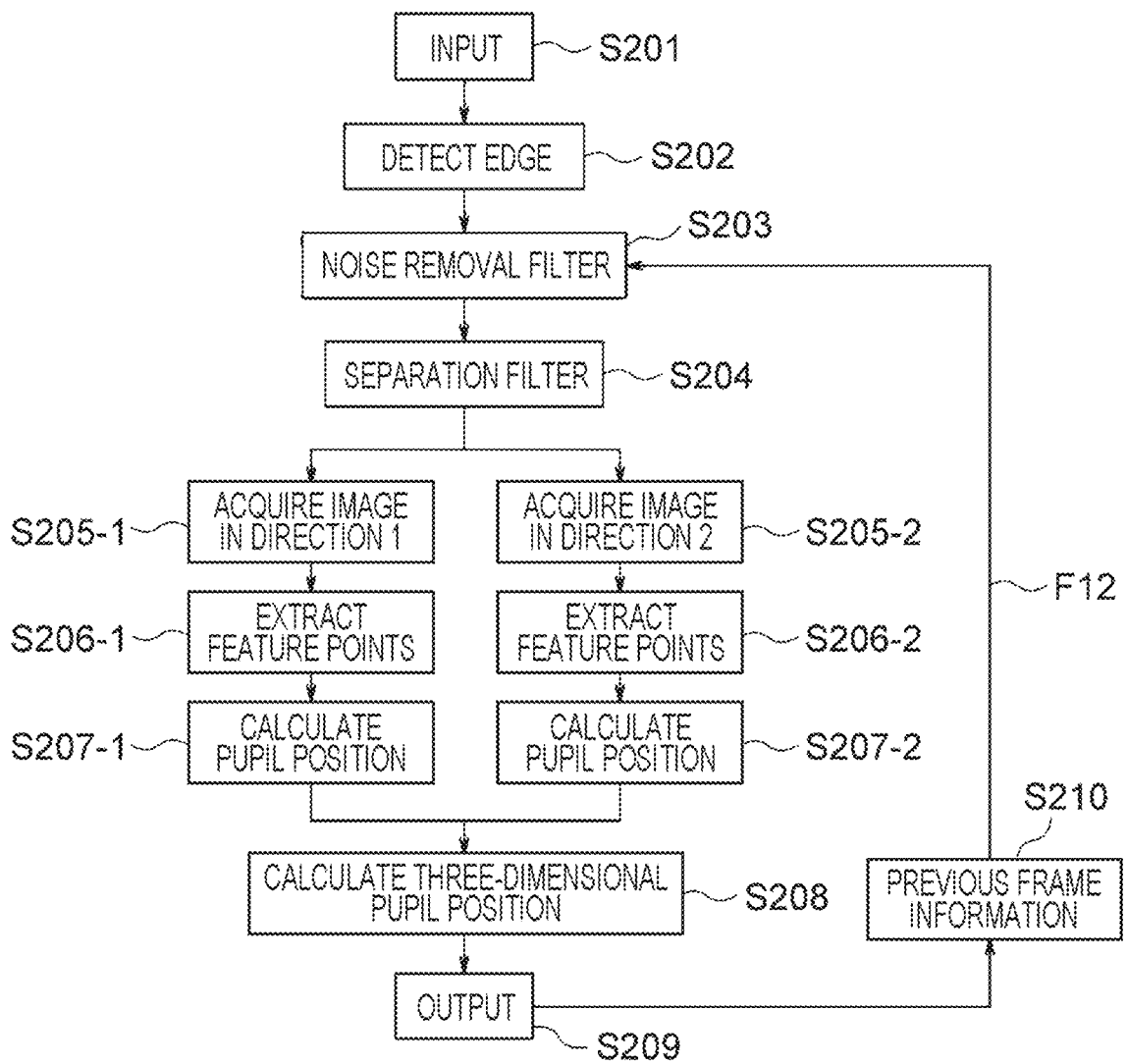
FIG. 12 is a diagram illustrating an example of a flow up to calculation of a three-dimensional eye (pupil) position using the line-of-sight detection device of the fourth embodiment to which the present technology is applied.

FIG. 12 is a diagram illustrating an example of a flow up to calculation of a three-dimensional eye (pupil) position using the line-of-sight detection device of the fourth embodiment according to the present technology.

In step S201 illustrated in FIG. 12, for example, image (video) information (image (video) information based on beams of reflected light in two directions (three or more directions may be used) from the eyeball simultaneously received by a camera (CMOS image sensor)) from a beam of reflected light from the optical axis of the eyeball and a beam of reflected light from the eyeball other than the beam of reflected light from the optical axis of the eyeball (for example, in two directions, but three or more directions may be used) is input.

In step S202, edge information of the image is detected. Examples of the edge information of the image include information of the boundary portion (edge portion) 43 between the pupil and the iris, information of the boundary portion 44 (edge portion) between the iris and the sclera, and information of the Purkinje image 41, and the like.

In step S203, noise removal is performed using the noise removal filter.

In step S204, the calculation unit included in the line-of-sight detection device of the fourth embodiment according to the present technology separates, for example, the image (video) information from the beam of reflected light from the optical axis of the eyeball and the image (video) information from the beam of reflected light from the eyeball other than the beam of reflected light from the optical axis of the eyeball using the separation filter.

In step S205-1, the separated image (video) information in direction 1 (for example, the beam of reflected light from the optical axis of the eyeball) is acquired.

In step S206-1, feature points are extracted from the image (video) information in direction 1 (for example, the beam of reflected light from the optical axis of the eyeball).

In step S207-1, for example, the eye (pupil) position is calculated by elliptical fitting using the image (video) information in direction 1 (for example, the beam of reflected light from the optical axis of the eyeball).

In step S205-2, the separated image (video) information in direction 2 (for example, the beam of reflected light from the eyeball other than the beam of reflected light from the optical axis of the eyeball) is acquired.

In step S206-2, feature points are extracted from image (video) information in direction 2 (for example, the beam of reflected light from the eyeball other than the beam of reflected light from the optical axis of the eyeball).

In step S207-2, for example, the eye (pupil) position is calculated by elliptical fitting using the image (video) information in direction 2 (for example, the beam of reflected light from the eyeball other than the beam of reflected light from the optical axis of the eyeball).

In step S208, coordinates of a three-dimensional eye (pupil) position are calculated from the amount of deviation between the eye (pupil) position obtained in step S207-1 and the eye (pupil) position obtained in step S207-2, and three-dimensional eye (pupil) positional information is output in step S209.

In a case where it is desired to use the information regarding the region of interest (ROI), the separation auxiliary data (data obtained when the images are separated in step S204, and the like), data regarding the feature point extraction in steps S206-1 and S206-2, and the like, which have been output in step S209, for the next frame as the previous frame information, the process proceeds to step S210. In step S210, as the previous frame information, the information regarding the region of interest (ROI), the separation auxiliary data (data obtained when the images are separated in step S204, and the like), the data regarding the feature point extraction in steps S206-1 and S206-2, and the like are fed back to step S203 (noise removal using the noise removal filter) (arrow F12).

As described above, the content described for the line-of-sight detection device of the fourth embodiment (Example 4 of the line-of-sight detection device) according to the present technology can be applied to the line-of-sight detection devices of the first to third embodiments according to the present technology described above and the line-of-sight detection devices of the fifth to seventh embodiments according to the present technology as described later unless there is a particular technical contradiction.

6. Fifth Embodiment (Example 5 of Line-of-Sight Detection Device)

A line-of-sight detection device of a fifth embodiment (Example 5 of the line-of-sight detection device) according to the present technology is a line-of-sight detection device including an imaging element, an illumination unit that illuminates an eyeball with a plurality of beams of illumination light, an optical element that guides respective beams of reflected light in a plurality of directions from the eyeball caused by the plurality of beams of illumination light to a direction of the imaging element, an optical system that causes the imaging element to non-selectively receive the beams of reflected light in the plurality of directions from the eyeball, and a calculation unit that converts, on the basis of the beams of reflected light in the plurality of directions from the eyeball received by the imaging element, the beams of reflected light into information of eyeball movement and/or positional information of a pupil. The imaging element included in the line-of-sight detection device of the fifth embodiment according to the present technology may be an imaging element (for example, DVS (Dynamic Vision Sensor)) having an event-driven function.

The calculation unit included in the line-of-sight detection device of the fifth embodiment according to the present technology can acquire a point group in a time direction by using each of pieces of information of beams of reflected light in at least two directions among pieces of information of the beams of reflected light in the plurality of directions from the eyeball received by the imaging element, and generates at least two optical flows, and separate the information of the beams of reflected light in the at least two directions into information of beams of reflected light in respective directions of the at least two directions according to a difference between the at least two optical flows. Then, the calculation unit included in the line-of-sight detection device of the fifth embodiment according to the present technology can convert the information into the information of the eyeball movement and/or the positional information of the pupil on the basis of the separated at least two pieces of information.

Hereinafter, the line-of-sight detection device of the fifth embodiment (Example 5 of the line-of-sight detection device) according to the present technology will be described with reference to FIGS. 13 to 15.

First, a line-of-sight detection device 1013 will be described with reference to FIG. 13.

The line-of-sight detection device 1013 includes a dynamic vision sensor (DVS) 1, an LED (illumination unit) 7 that illuminates an eyeball with a plurality of (for example, two) beams of illumination light, optical elements 513 and 613 that guide a first beam of reflected light L13-1 (beams of light from optical axes of the eyeballs 500-1 and 500-2) and a second beam of reflected light L13-2 from the eyeball 500 (the eyeballs 500-1 and 500-2) caused by the plurality of (for example, two) beams of illumination light to a direction of the dynamic vision sensor (DVS) 1, and an optical system (not illustrated) that causes the dynamic vision sensor (DVS) 1 to non-selectively receive the first beam of reflected light L13-1 and the second beam of reflected light L13-2 in two directions from the eyeball 500 (the eyeballs 500-1 and 500-2), and a calculation unit (not illustrated) that converts, on the basis of the first beam of reflected light L13-1 and the second beam of reflected light L13-2 in two directions from the eyeball 500 (the eyeballs 500-1 and 500-2) received by the dynamic vision sensor (DVS) 1, the beams of reflected light into information of movement of the eyeball 500 (the eyeballs 500-1 and 500-2) and/or positional information of a pupil. The optical system can cause the dynamic vision sensor (DVS) 1 to non-selectively receive the first beam of reflected light L13-1 and the second beam of reflected light L13-2 in two directions from the eyeball 500-1 or the eyeball 500-2 without spatial assignment.

The first optical element 513 is the HOE (holographic optical element) grating (hologram diffraction grating), and the second optical element 613 is the HOE (holographic optical element) mirror (hologram mirror). Note that the first optical element 513 may be the HOE (holographic optical element) mirror (hologram mirror), the second optical element 613 may be the HOE (holographic optical element) mirror (hologram mirror), and the first optical element 513 and/or the first optical element 613 may be a mirror (for example, a half mirror).

The first optical element 513 and the second optical element 613 are disposed on the substrate 4. The substrate 4 may be a transparent substrate or an impermeable substrate. The substrate 4 is, for example, a light guide plate, a glass plate, or the like.

In the line-of-sight detection device 1013, the beams of reflected light in two directions (the first beam of reflected light L5-1 and the second beam of reflected light L5-2) from the eyeball 500 (the eyeballs 500-1 and 500-2) has been described, but the line-of-sight detection device 1013 can also be applied to the beams of reflected light in three or more directions from the eyeball 500 (the eyeballs 500-1 and 500-2).

Figure 13:
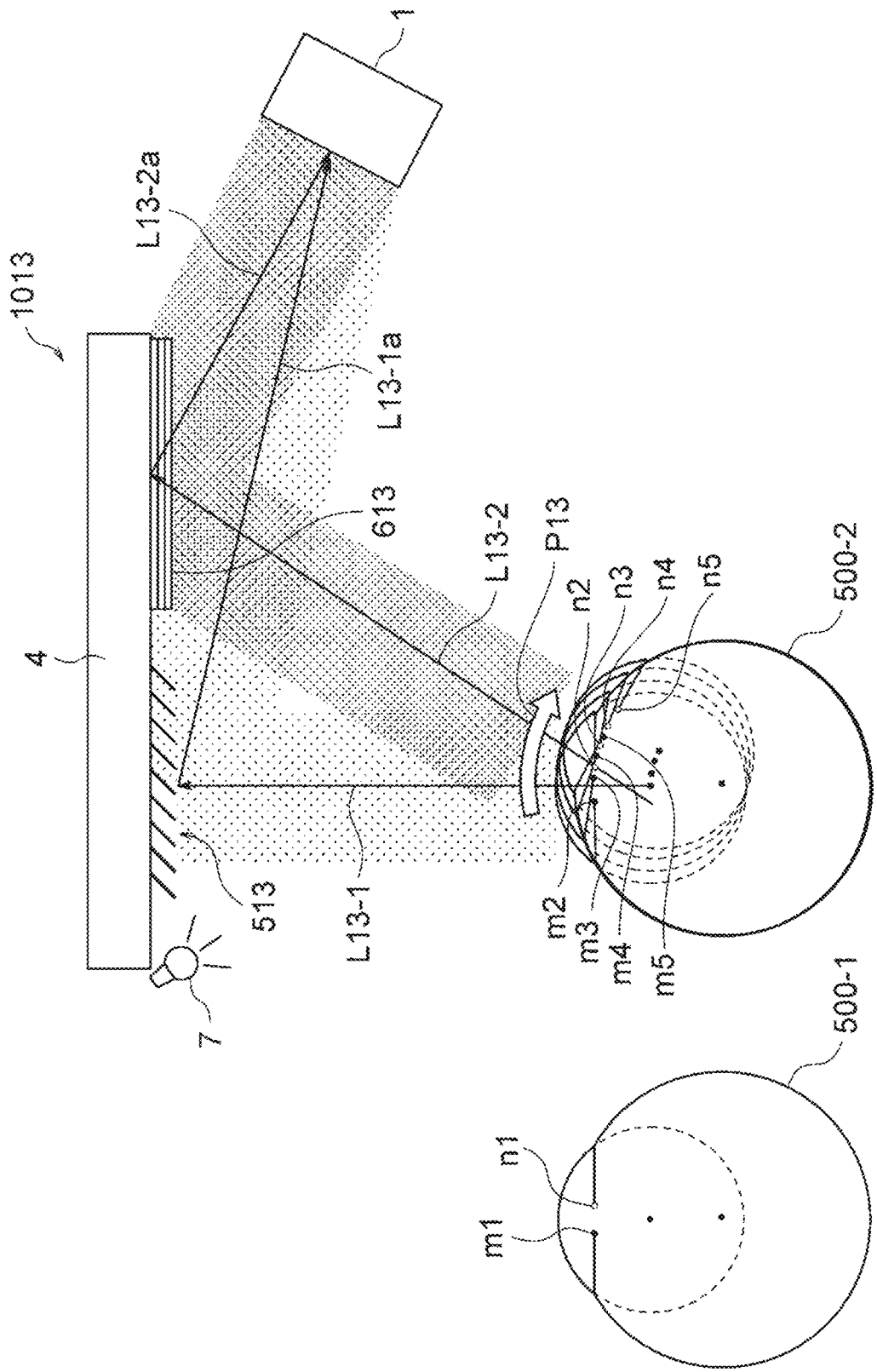
FIG. 13 is a diagram illustrating a configuration example of a line-of-sight detection device of a fifth embodiment to which the present technology is applied.

As illustrated in FIG. 13, the eyeball 500-2 is an eyeball resulted from rotating the eyeball 500-1 to the right (arrow P13 in FIG. 13). More specifically, a left boundary portion (left edge portion) m1 between the pupil and the iris of the eyeball 500-1 and left boundary portions (left edge portions) m2, m3, m4, and m5 between the pupil and the iris of the eyeball 500-2 rotate to the right (arrow P13) in this order. Similarly, a right boundary portion (left edge portion) n1 between the pupil and the iris of the eyeball 500-1 and left boundary portions (right edge portions) n2, n3, n4, and n5 between the pupil and the iris of the eyeball 500-2 rotate to the right (arrow P13) in this order.

Figure 14:
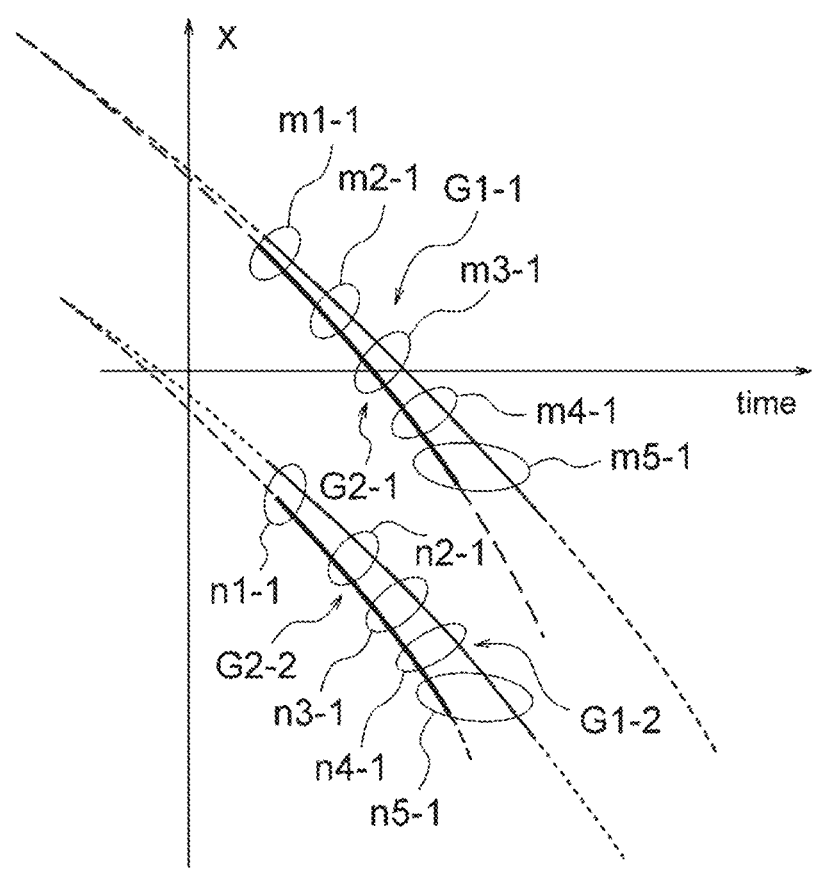
FIG. 14 is a diagram for describing a method of accumulating information (edge information) of beams of reflected light in a plurality of directions (two directions) in a time direction and detecting a plane of a trajectory based on accumulated data to thereby perform image separation, using the line-of-sight detection device of the fifth embodiment to which the present technology is applied.

FIG. 14 is a diagram for describing a method of performing image separation using the line-of-sight detection device of the fifth embodiment according to the present technology, and more specifically, is a graph in which a horizontal axis is time (time) and a vertical axis is a position (x) of a boundary portion (edge portion) between the pupil and the iris.

A line G1-1 illustrated in FIG. 14 is a trajectory (optical flow) of the left boundary portion (left edge portion) between the pupil and the iris by the first beam of reflected light L13-1, and a line G2-1 is a trajectory (optical flow) of the left boundary portion (left edge portion) between the pupil and the iris by the second beam of reflected light L13-2. The G1-1 line and the G2-1 line are separate and independent lines, that is, trajectories (optical flows) independent from each other. On the lines G1-1 and G2-1, a circular region m1-1 corresponds to the left boundary portion (left edge portion) m1 between the pupil and the iris, a circular region m2-1 corresponds to the left boundary portion (left edge portion) m2 between the pupil and the iris, a circular region m3-1 corresponds to the left boundary portion (left edge portion) m3 between the pupil and the iris, a circular region m4-1 corresponds to the left boundary portion (left edge portion) m4 between the pupil and the iris, and a circular region m5-1 corresponds to the left boundary portion (left edge portion) m5 between the pupil and the iris. A broken line extending from the circular region m1-1 of the lines G1-1 and G2-1 is a prediction of the trajectory of the left boundary portion (left edge portion) between the pupil and the iris when the eyeball 500-1 is further rotated to the left from the left boundary portion (left edge portion) m1 between the pupil and the iris. A broken line extending from the circular region m5-1 of the lines G1-1 and G2-1 is a prediction of the trajectory of the left boundary portion (left edge portion) between the pupil and the iris when the eyeball 500-2 is further rotated to the right from the left boundary portion (left edge portion) m5 between the pupil and the iris.

A line G1-2 illustrated in FIG. 14 is a trajectory (optical flow) of the right boundary portion (right edge portion) between the pupil and the iris by the first beam of reflected light L13-1, and a line G2-2 is a trajectory (optical flow) of the right boundary portion (left edge portion) between the pupil and the iris by the second beam of reflected light L13-2. The line G1-2 and the line G2-2 are separate and independent lines, that is, trajectories (optical flows) independent from each other. On the lines G1-2 and G2-2, a circular region n1-1 corresponds to the right boundary portion (right edge portion) n1 between the pupil and the iris, a circular region n2-1 corresponds to the right boundary portion (left edge portion) n2 between the pupil and the iris, a circular region n3-1 corresponds to the right boundary portion (right edge portion) n3 between the pupil and the iris, a circular region n4-1 corresponds to the right boundary portion (right edge portion) n4 between the pupil and the iris, and a circular region n5-1 corresponds to the right boundary portion (right edge portion) n5 between the pupil and the iris. A broken line extending from the circular region n1-1 of the lines G1-2 and G2-2 is a prediction of the trajectory of the right boundary portion (left edge portion) between the pupil and the iris when the eyeball 500-1 is further rotated to the left from the right boundary portion (right edge portion) n1 between the pupil and the iris. A broken line extending from the circular region n5-1 of the lines G1-2 and G2-2 is a prediction of the trajectory of the left boundary portion (left edge portion) between the pupil and the iris when the eyeball 500-2 is further rotated to the right from the right boundary portion (right edge portion) n5 between the pupil and the iris.

In summary, the edge information is accumulated in the time direction from two directions, and the plane of the trajectory is detected, whereby the image separation can be performed.

FIG. 15 is a diagram illustrating an example of a flow up to calculation of a three-dimensional eye (pupil) position using the line-of-sight detection device of the fifth embodiment according to the present technology.

In step S2001 illustrated in FIG. 15, for example, image (video) information (image (video) information based on beams of reflected light in two directions (three or more directions may be used) from the eyeball simultaneously received by DVS) from a beam of reflected light from the optical axis of the eyeball and a beam of reflected light from the eyeball other than the beam of reflected light from the optical axis of the eyeball (for example, in two directions, but three or more directions may be used) is input.

In step S2002, the event information generated in a predetermined fixed period is accumulated.

In step S2003, noise removal is performed using the noise removal filter.

In step S2004, the calculation unit included in the line-of-sight detection device of the fifth embodiment according to the present technology separates, for example, the image (video) information from the beam of reflected light from the optical axis of the eyeball and the image (video) information from the beam of reflected light from the eyeball other than the beam of reflected light from the optical axis of the eyeball using the separation filter.

In step S2005-1, the separated image (video) information in direction 1 (for example, the beam of reflected light from the optical axis of the eyeball) is acquired.

In step S2006-1, feature points are extracted from the image (video) information in direction 1 (for example, the beam of reflected light from the optical axis of the eyeball).

In step S2007-1, for example, the eye (pupil) position is calculated by elliptical fitting using the image (video) information in direction 1 (for example, the beam of reflected light from the optical axis of the eyeball).

In step S2005-2, the separated image (video) information in direction 2 (for example, the beam of reflected light from the eyeball other than the beam of reflected light from the optical axis of the eyeball) is acquired.

In step S2006-2, feature points are extracted from image (video) information in direction 2 (for example, the beam of reflected light from the eyeball other than the beam of reflected light from the optical axis of the eyeball).

In step S2007-2, for example, the eye (pupil) position is calculated by elliptical fitting using the image (video) information in direction 2 (for example, the beam of reflected light from the eyeball other than the beam of reflected light from the optical axis of the eyeball).

In step S2008, coordinates of a three-dimensional eye (pupil) position are calculated from the amount of deviation between the eye (pupil) position obtained in step S2007-1 and the eye (pupil) position obtained in step S2007-2, and three-dimensional eye (pupil) positional information is output in step S2009.

In a case where it is desired to use the information regarding the region of interest (ROI), the separation auxiliary data (data obtained when the images are separated in step S2004, and the like), data regarding the feature point extraction in steps S2006-1 and S2006-2, and the like, which have been output in step S2009, for the next frame as the information regarding the trajectory up to the previous frame, the process proceeds to step S2010. In step S2010, as the information of the trajectory up to the previous frame, information regarding the region of interest (ROI), the separation auxiliary data (data obtained when the images are separated in step S2004, and the like), the data regarding the feature point extraction in steps S2006-1 and S2006-2, and the like are fed back to step S2003 (noise removal using the noise removal filter) (arrow F15).

As described above, the content described for the line-of-sight detection device of the fifth embodiment (Example 5 of the line-of-sight detection device) according to the present technology can be applied to the line-of-sight detection devices of the first to fourth embodiments according to the present technology described above and the line-of-sight detection devices of the sixth and seventh embodiments according to the present technology as described later unless there is a particular technical contradiction.

7. Sixth Embodiment (Example 6 of Line-of-Sight Detection Device)

A line-of-sight detection device of a sixth embodiment (Example 6 of the line-of-sight detection device) according to the present technology is a line-of-sight detection device including an imaging element, an illumination unit that illuminates an eyeball with a plurality of beams of illumination light, an optical element that guides respective beams of reflected light in a plurality of directions from the eyeball caused by the plurality of beams of illumination light to a direction of the imaging element, an optical system that causes the imaging element to non-selectively receive the beams of reflected light in the plurality of directions from the eyeball, and a calculation unit that converts, on the basis of the beams of reflected light in the plurality of directions from the eyeball received by the imaging element, the beams of reflected light into information of eyeball movement and/or positional information of a pupil. The imaging element included in the line-of-sight detection device of the sixth embodiment according to the present technology may be an imaging element (for example, DVS (Dynamic Vision Sensor)) having an event-driven function.

The optical element included in the line-of-sight detection device of the sixth embodiment according to the present technology can cause a difference in aberration of reflected light in at least two directions among reflected light in a plurality of directions from the eyeball.

A calculation unit included in a line-of-sight detection device of a sixth embodiment according to the present technology includes a low-pass filter and a high-pass filter. The calculation unit included in the line-of-sight detection device of the sixth embodiment according to the present technology can perform Fourier transform on information of beams of reflected light in at least two directions received by the imaging element, and separate information of the beams of reflected light in the at least two directions into information of beams of reflected light in respective directions of at least two directions according to a difference in aberration obtained by the optical element using a low-pass filter and a high-pass filter. Then, the calculation unit included in the line-of-sight detection device of the sixth embodiment according to the present technology can convert the information into the information of the eyeball movement and/or the positional information of the pupil on the basis of the separated at least two pieces of information.

Hereinafter, the line-of-sight detection device of the sixth embodiment (Example 6 of the line-of-sight detection device) according to the present technology will be described with reference to FIGS. 16A, 16B, and 17.

First, description will be made with reference to FIGS. 16A and 16B. FIGS. 16A and 16B are diagrams schematically illustrating an image when sensing of the eyeball is performed using the line-of-sight detection device of the sixth embodiment according to the present technology, and more specifically, FIG. 16A is a diagram illustrating an image of the DVS based on, for example, information of light in which aberration is imparted to the beam of reflected light from the optical axis of the eyeball by the optical element, and FIG. 16B is a diagram illustrating an image of the DVS based on, for example, information of light in which aberration is imparted to the beam of reflected light from the eyeball other than the beam of reflected light from the optical axis of the eyeball by the optical element. As illustrated in FIGS. 16A and 16B, the image in FIG. 16A has a larger amount of blurring at the boundary portion (edge portion) 43 between the pupil and the iris, the boundary portion 44 (edge portion) between the iris and the sclera, the Purkinje image 41, and the like as compared to the image in FIG. 16B. Note that, although not illustrated, for example, the two optical elements used in FIGS. 16A and 16B may be replaced so that the image in FIG. 16B has a larger blur amount at the boundary portion (edge portion) 43 between the pupil and the iris, the boundary portion 44 (edge portion) between the iris and the sclera, the Purkinje image 41, and the like as compared to the image in FIG. 16A.

Figure 17:
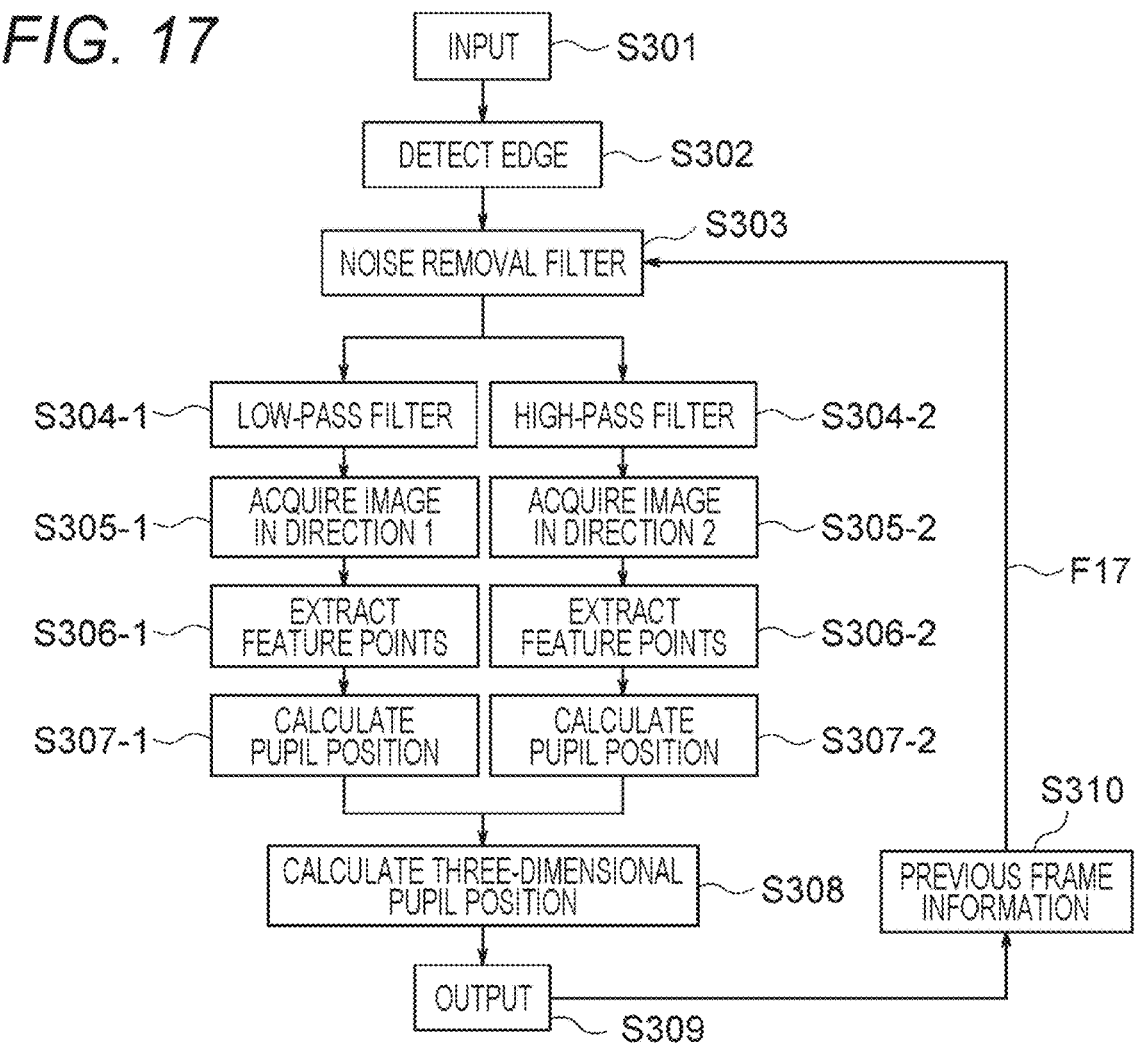
FIG. 17 is a diagram illustrating an example of a flow up to calculation of the three-dimensional eye (pupil) position using the line-of-sight detection device of the sixth embodiment to which the present technology is applied.

FIG. 17 is a diagram illustrating an example of a flow up to calculation of a three-dimensional eye (pupil) position using the line-of-sight detection device of the sixth embodiment according to the present technology.

In step S301 illustrated in FIG. 17, for example, image (video) information (image (video) information based on beams of reflected light in two directions (three or more directions may be used) from the eyeball simultaneously received by DVS) from a beam of reflected light from the optical axis of the eyeball and a beam of reflected light from the eyeball other than the beam of reflected light from the optical axis of the eyeball (for example, in two directions, but three or more directions may be used) is input.

In step S302, edge information of the image is detected. Examples of the edge information of the image include information of the boundary portion (edge portion) 43 between the pupil and the iris, information of the boundary portion 44 (edge portion) between the iris and the sclera, and information of the Purkinje image 41, and the like.

In step S303, noise removal is performed using the noise removal filter.

Fourier transform is performed, and next, in step S304-1, image (video) information in direction 1 (for example, from the beam of reflected light from the optical axis of the eyeball) is acquired using the low-pass filter in the calculation unit included in the line-of-sight detection device of the sixth embodiment according to the present technology (S305-1).

In step S306-1, feature points are extracted from image (video) information in direction 1 (for example, from the beam of reflected light from the optical axis of the eyeball).

In step S307-1, for example, the eye (pupil) position is calculated by elliptical fitting using the image (video) information in direction 1 (for example, from the beam of reflected light from the optical axis of the eyeball).

Fourier transform is performed, and next, in step S304-2, image (video) information in direction 2 (for example, from the beam of reflected light from the eyeball other than the beam of reflected light from the optical axis of the eyeball) is acquired using the high-pass filter in the calculation unit included in the line-of-sight detection device of the sixth embodiment according to the present technology (S305-2). Note that step 304-1 (image separation using a low-pass filter) and step 304-2 (image separation using a high-pass filter) described above may be performed simultaneously.

In step S306-2, feature points are extracted from image (video) information in direction 2 (for example, the beam of reflected light from the eyeball other than the beam of reflected light from the optical axis of the eyeball).

In step S307-2, for example, the eye (pupil) position is calculated by elliptical fitting using the image (video) information in direction 2 (for example, the beam of reflected light from the eyeball other than the beam of reflected light from the optical axis of the eyeball).

In step S308, coordinates of a three-dimensional eye (pupil) position are calculated from the amount of deviation between the eye (pupil) position obtained in step S307-1 and the eye (pupil) position obtained in step S307-2, and three-dimensional eye (pupil) positional information is output in step S309.

In a case where it is desired to use the information regarding the region of interest (ROI), data regarding the feature point extraction in steps S306-1 and 306-2, and the like, which have been output in step S309, for the next frame as the previous frame information, the process proceeds to step S310. In step 310, as the previous frame information, the information regarding the region of interest (ROI), the data regarding the feature point extraction in steps S306-1 and 306-2, and the like are fed back to step S303 (noise removal using the noise removal filter) (arrow F16).

As described above, the content described for the line-of-sight detection device of the sixth embodiment (Example 6 of the line-of-sight detection device) according to the present technology can be applied to the line-of-sight detection devices of the first to fifth embodiments according to the present technology described above and the line-of-sight detection device of the seventh embodiment according to the present technology as described later unless there is a particular technical contradiction.

8. Seventh Embodiment (Example 7 of Line-of-Sight Detection Device)

A line-of-sight detection device of a seventh embodiment (Example 7 of the line-of-sight detection device) according to the present technology is a line-of-sight detection device including an imaging element, an illumination unit that illuminates an eyeball with a plurality of beams of illumination light, an optical element that guides respective beams of reflected light in a plurality of directions from the eyeball caused by the plurality of beams of illumination light to a direction of the imaging element, an optical system that causes the imaging element to non-selectively receive the beams of reflected light in the plurality of directions from the eyeball, and a calculation unit that converts, on the basis of the beams of reflected light in the plurality of directions from the eyeball received by the imaging element, the beams of reflected light into information of eyeball movement and/or positional information of a pupil. The imaging element included in the line-of-sight detection device of the first embodiment according to the present technology may be an imaging element (for example, DVS (Dynamic Vision Sensor)) having an event-driven function.

The calculation unit included in the line-of-sight detection device of the seventh embodiment according to the present technology can separate information of the beams of reflected light in the plurality of directions from the eyeball received by the imaging element into information of beams of reflected light in respective directions of the plurality of directions from the eyeball received by the imaging element by using a deep neural network (DNN). Then, the calculation unit included in the line-of-sight detection device of the seventh embodiment according to the present technology can convert the information into the information of the eyeball movement and/or the positional information of the pupil on the basis of each of the separated pieces of the information.

Hereinafter, the line-of-sight detection device of the seventh embodiment (Example 7 of the line-of-sight detection device) according to the present technology will be described with reference to FIG. 18.

Figure 18:
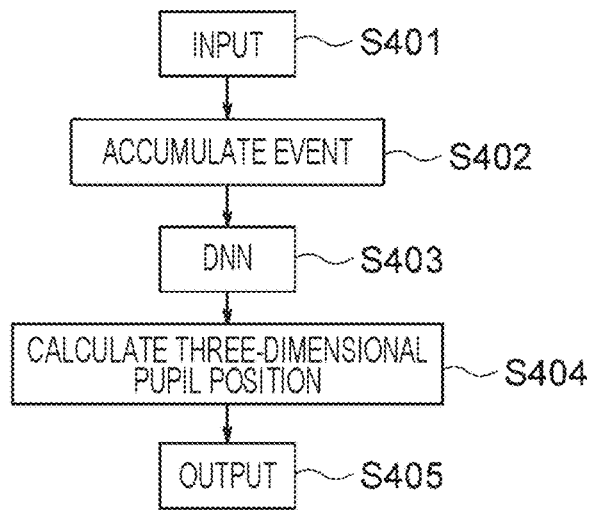
FIG. 18 is a diagram illustrating an example of a flow up to calculation of the three-dimensional eye (pupil) position using a line-of-sight detection device of a seventh embodiment to which the present technology is applied.

FIG. 18 is a diagram illustrating an example of a flow up to calculation of a three-dimensional eye (pupil) position using the line-of-sight detection device of the seventh embodiment according to the present technology.

In step S401 illustrated in FIG. 18, for example, image (video) information (image (video) information based on beams of reflected light in two directions (three or more directions may be used) from the eyeball simultaneously received by DVS) from a beam of reflected light from the optical axis of the eyeball and a beam of reflected light from the eyeball other than the beam of reflected light from the optical axis of the eyeball (for example, in two directions, but three or more directions may be used) is input.

In step S402, the event information generated in a predetermined fixed period is accumulated.

In step S403, the calculation unit included in the line-of-sight detection device of the seventh embodiment according to the technology separates the image (video) information from the beam of reflected light from the optical axis of the eyeball and the image (video) information from the beam of reflected light from the eyeball other than the beam of reflected light from the optical axis of the eyeball using deep learning as an algorithm, then extracts feature points from the image (video) information in direction 1 (for example, from the beam of reflected light from the optical axis of the eyeball) and the image (video) information in direction 2 (for example, the beam of reflected light from the eyeball other than the beam of reflected light from the optical axis of the eyeball), and finally calculates the eye (pupil) position using the image (video) information in direction 1 (for example, from the beam of reflected light from the optical axis of the eyeball) and the image (video) information in direction 2 (for example, the beam of reflected light from the eyeball other than the beam of reflected light from the optical axis of the eyeball).

In step S404, coordinates of a three-dimensional eye (pupil) position are calculated from the amount of deviation between the eye (pupil) position based on the image (video) information in direction 1 (for example, from the beam of reflected light from the optical axis of the eyeball) and the position based on the image (video) information in direction 2 (for example, the beam of reflected light from the eyeball other than the beam of reflected light from the optical axis of the eyeball) obtained in step S403, and three-dimensional eye (pupil) positional information is output in step S409.

As described above, the content described for the line-of-sight detection device of the seventh embodiment (Example 7 of the line-of-sight detection device) according to the present technology can be applied to the line-of-sight detection devices of the first to sixth embodiments according to the present technology described above unless there is a particular technical contradiction.

9. Eighth Embodiment (Example 1 of Display Device)

A display device of an eighth embodiment (Example 1 of display device) according to the present technology is a display device including at least the line-of-sight detection device of one embodiment among the line-of-sight detection devices of the first to seventh embodiments according to the present technology.

Figure 20:
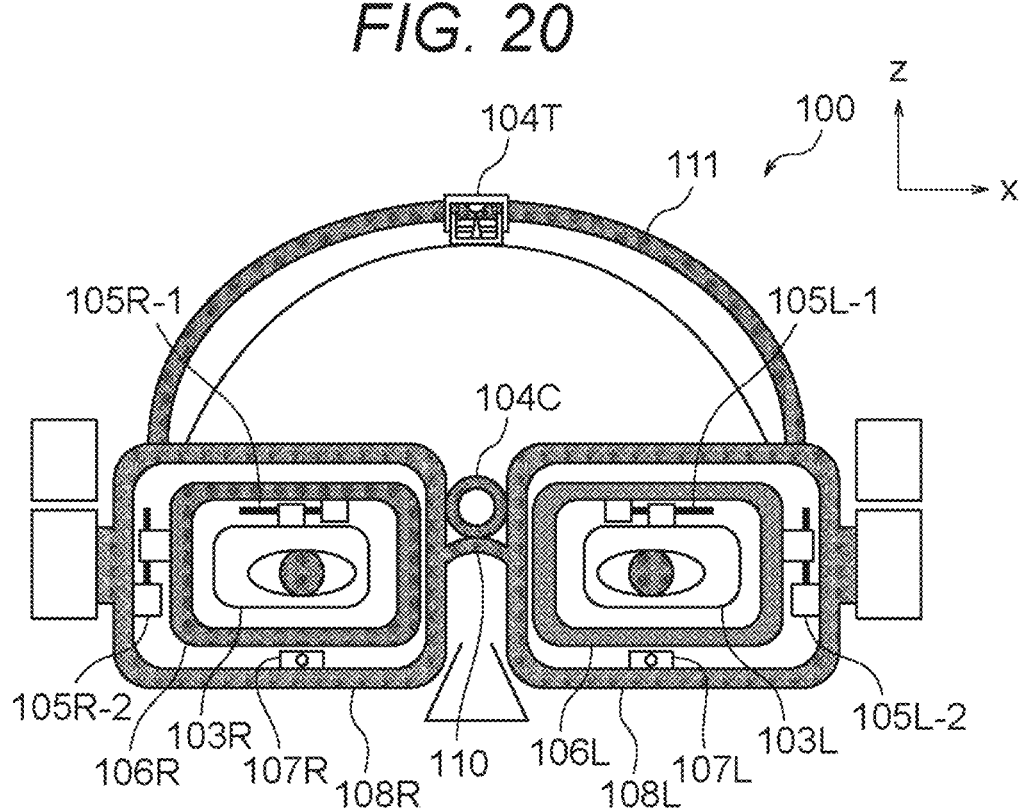
FIG. 20 is a front view illustrating a configuration example of the display device of the eighth embodiment to which the present technology is applied.
Figure 21:
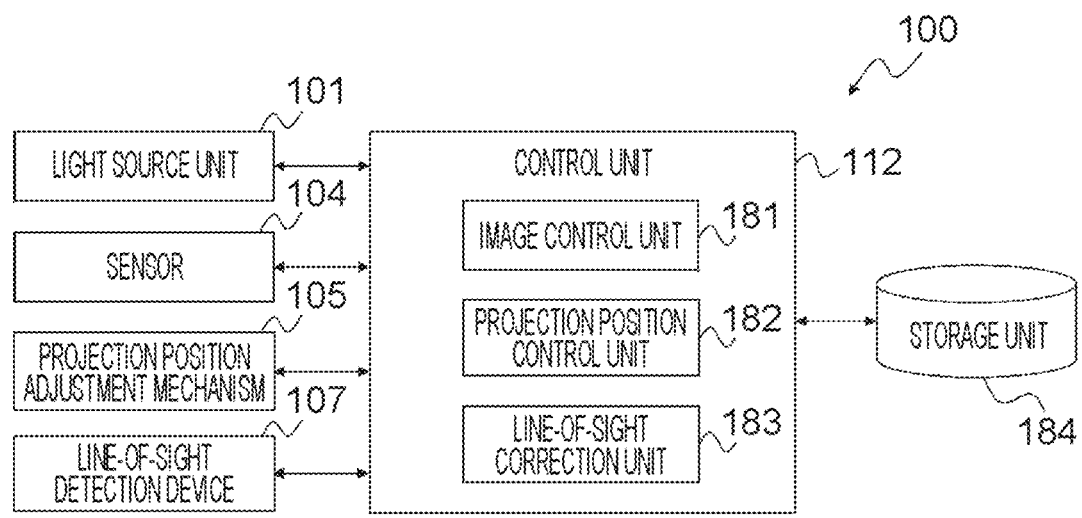
FIG. 21 is a block diagram illustrating a configuration example of the display device of the eighth embodiment to which the present technology is applied.

Hereinafter, the display device of the eighth embodiment (Example 1 of the display device) according to the present technology will be described with reference to FIGS. 19 to 21.

First, a configuration example of the display device of the eighth embodiment according to the present technology will be described with reference to FIGS. 19 and 20. FIG. 19 is a top view of the display device according to the present technology worn on the head of the user. FIG. 20 is a front view of the display device according to the present technology worn on the head of the user. The display device illustrated in FIG. 19 includes a video display unit (also referred to as an image display unit), a sensor (in the present description, a sensor that detects a change in the position of the display device with respect to the head is also referred to as a "displacement sensor" or a "sensor") that detects a change in position of the display device with respect to the head, a line-of-sight detection device (a line-of-sight detection device of one embodiment of the line-of-sight detection devices of the first to seventh embodiments according to the present technology, and the same applies hereinafter), a projection position adjustment mechanism, a control unit, and a storage unit. These components will be described below.

(Video Display Unit)

Figure 19:
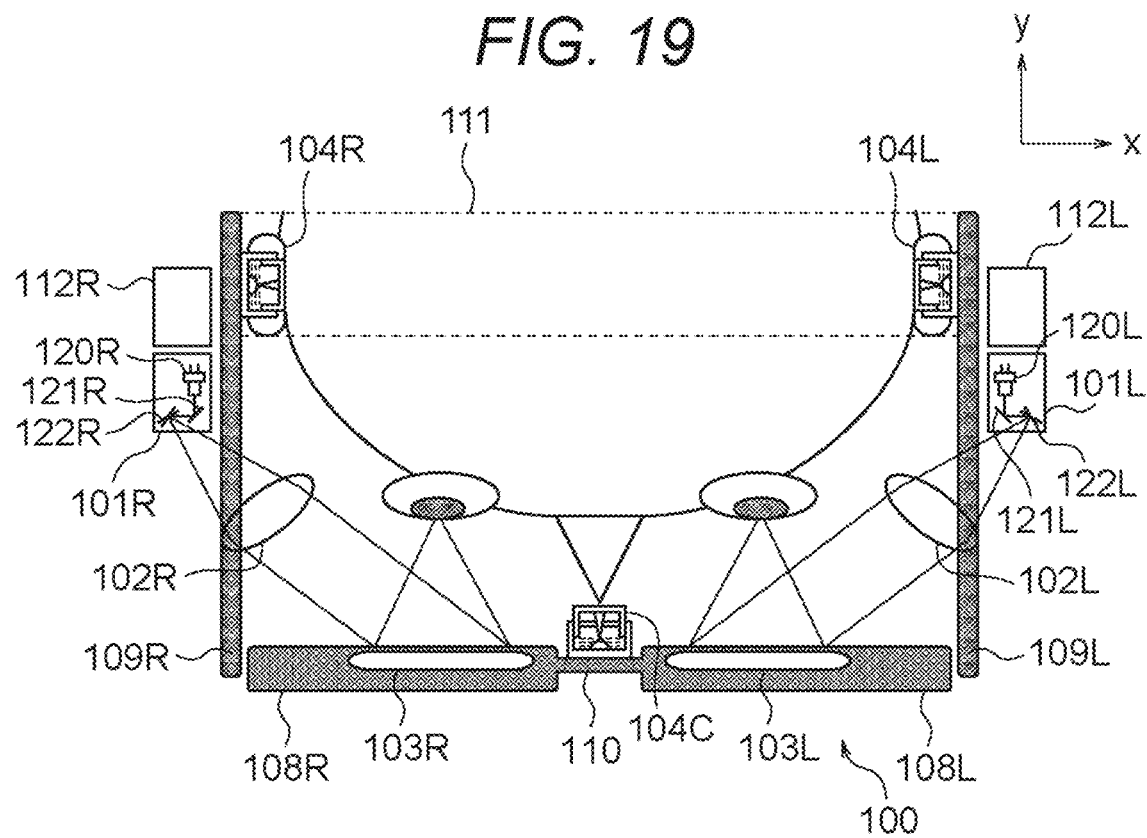
FIG. 19 is a top view illustrating a configuration example of a display device of an eighth embodiment to which the present technology is applied.

As illustrated in FIG. 19, a display device 100 has an eyeglass-like shape, and is configured to project video display light (which may be referred to as image display light) to each of both eyes. That is, the display device 100 includes a video display unit that projects video display light to the left eye and a video display unit that projects video display light to the right eye. The video display unit that projects video display light to the left eye includes a light source unit 101L, a projection optical system 102L, and a holographic optical element (hereinafter, also referred to as HOE) 103L.

The light source unit 101L emits video display light. As a configuration for emitting the video display light, the light source unit 101L can include, for example, a laser light source 120L, a mirror 121L, and a scanning mirror 122L. Laser light emitted from the laser light source 120L is reflected by mirror 121L, and then reaches the scanning mirror 122L. The scanning mirror 122L two-dimensionally scans the laser light. The scanning mirror 122L may be, for example, a MEMS mirror. The scanning mirror 122L can move the direction of the laser light at a high speed so that an image is formed on the retina.

The projection optical system 102L adjusts the direction of the video display light so that the video display light reaches a desired region and/or position of the HOE 103L. For example, the video display light scanned by the scanning mirror 122L is converted into parallel light.

The HOE 103L diffracts such that the video display light is condensed near the pupil of the user and is emitted to the retina. The HOE 103L may be, for example, a reflection type diffraction element. The HOE 103L may have an optical characteristic of functioning as a lens for light in a wavelength range of the video display light and transmitting light having a wavelength outside the wavelength range. With the optical characteristic, the user can recognize a landscape ahead in the line-of-sight direction via the HOE 103L, for example, and can recognize an image by the video display light. That is, the image by the video display light can be superimposed on the landscape of the outside world. Examples of the HOE 103L may include a hologram lens, preferably a film-shaped hologram lens, and more preferably a transparent film-shaped hologram lens. The film-shaped hologram lens may be used by being attached to, for example, glass or the like. The desired optical characteristics can be imparted to the hologram lens by techniques known in the art. Then, as the hologram lens, a commercially available hologram lens may be used, or the hologram lens may be manufactured by a technique known in the art.

As described above, the light source unit 101L, the projection optical system 102L, and the HOE 103L cause the video display light to reach the left eye of the user.

The display device 100 includes a temple portion 109L and a rim portion 108L which are a part of the eyeglass shape. The light source unit 101L and the projection optical system 102L are arranged on the temple portion 109L. The HOE 103L is held on the rim portion 108L. More specifically, an inner rim portion 106L is held by the rim portion 108L with a projection position adjustment mechanism 105L-2 interposed therebetween, and the HOE 103L is held by the inner rim portion 106L with a projection position adjustment mechanism 105L-1 interposed therebetween.

The video display unit that projects video display light to the right eye of the user includes a light source unit 101R, a projection optical system 102R, and an HOE 103R.

The description of the light source unit 101L, the projection optical system 102L, and the HOE 103L also applies to the light source unit 101R, the projection optical system 102R, and the HOE 103R.

Similarly to the video display unit for the left eye, the light source unit 101R and the projection optical system 102R are arranged in the temple portion 109R. The HOE 103R is held on a rim portion 108R. More specifically, an inner rim portion 106R is held on the rim portion 108R with a projection position adjustment mechanism 105R-2 interposed therebetween, and the HOE 103R is held by the inner rim portion 106R with a projection position adjustment mechanism 105R-1 interposed therebetween.

The rim portions 108L and 108R of the display device 100 are connected to each other via a bridge portion 110. The bridge portion 110 is a portion that is put on the nose of the user when the user wears the display device 100. Furthermore, both the rim portions 108L and 108R of the display device 100 are connected to a headband portion 111. As illustrated in FIG. 20, the headband portion 111 is a portion that comes into contact with the top of the head of the user when the user wears the display device 100.

The light source unit 101L illustrated in FIG. 19 includes one laser light source 120L, but the number of laser light sources included in the light source unit 101L may be two or more, and may be, for example, two to five. The plurality of laser light sources may output laser lights having different wavelengths. Similarly, the light source unit 101R includes one laser light source 120R, but the number of laser light sources included in the light source unit 101R may be two or more, and may be, for example, two to five. The plurality of laser light sources may output laser lights having different wavelengths. By using the laser light source 120L and the laser light source 120R, a stimulus of a specific wavelength can be presented.

Although not illustrated, the display device 100 may further include a wavelength dispersion compensation member. The wavelength dispersion compensation member is, for example, a reflection type or transmission type volume hologram, a reflection type or transmission type relief hologram, or the like. The wavelength dispersion compensation member may be disposed around the mirror 121L and/or 121R, for example, between the mirror 121L and the scanning mirror 122L and/or between the mirror 121R and the scanning mirror 122R. When the wavelength dispersion compensation member is used for the display device 100, it is possible to accurately stimulate an arbitrary point (predetermined point) on the retina because wavelength dispersion is compensated.

(Sensor)

The display device 100 further includes sensors 104L, 104R, 104C, and 104T that detect a change in the position of the display device 100 with respect to the head of the user. The change in position detected by these sensors may be, for example, a direction of change in position and/or an amount of change in position. Note that, in the present description, the sensors 104L, 104R, 104C, and 104T may be collectively referred to as a sensor 104.

The sensors 104L and 104R detect a position change of the display device 100 with respect to the user's head in the horizontal direction, the sensor 104C detects a position change of the display device 100 with respect to the user's head in the front-rear direction, and the sensor 104T detects a position change of the display device 100 with respect to the user's head in the vertical direction. Thus, an attachment deviation can be three-dimensionally grasped.

(Line-of-Sight Detection Device)

The display device 100 includes line-of-sight detection devices 107L and 107R that detect the line of sight of the user. In the present description, the line-of-sight detection devices 107L and 107R may be collectively referred to as a line-of-sight detection device 107. The line-of-sight detection device of one embodiment of the line-of-sight detection devices of the first to seventh embodiments according to the present technology described above can be applied to the line-of-sight detection device 107 (the line-of-sight detection devices 107L and 107R).

(Projection Position Adjustment Mechanism)

The projection position adjustment mechanisms 105L-1 and 105L-2 and 105R-1 and 105R-2 that adjust the projection position of the video display light emitted from the display device 100 can be further included. Note that, in the present description, these four projection position adjustment mechanisms may be collectively referred to as a projection position adjustment mechanism 105. The projection position adjustment mechanism 105 may be configured to adjust the projection position of the video display light following the line of sight, for example. The projection position adjustment mechanism 105 can adjust the projection position of the video display light according to the attachment deviation.

In addition, the projection position adjustment mechanism 105 can adjust the projection position of the video display light according to rotational movement of the eyeball or movement of the line of sight. For example, when the display device 100 includes the projection position adjustment mechanism 105, the position of the image to be presented to the user can be adjusted to a more appropriate position. For example, in a case where an image presented by the display device 100 is superimposed on an image of the outside world, it is possible to display the image at a more appropriate position by detecting the line of sight of the user. That is, inclusion of the line-of-sight detection device 107 is preferable for presentation of the AR information. Furthermore, by these projection position adjustment mechanisms, it is also possible to adjust the position where the video display light is condensed in the image display in a Maxwell view.

The projection position adjustment mechanisms 105L-1 and 105L-2 adjust the projection position of the video display light projected on the left eye. The projection position adjustment mechanism 105L-1 adjusts the positional relationship between the inner rim portion 106L and the rim portion 108L in a z-axis direction. For example, the projection position adjustment mechanism 105L-1 moves the inner rim portion 106L in the z-axis direction with respect to the rim portion 108L. Thus, the position of the HOE 103L in the z-axis direction is adjusted. The projection position adjustment mechanism 105L-2 adjusts the positional relationship between the HOE 103L and the inner rim portion 106L in an x-axis direction. For example, the projection position adjustment mechanism 105L-2 moves the HOE 103L in the x-axis direction with respect to the inner rim portion 106L. Thus, the position of the HOE 103L in the x-axis direction is adjusted.

The drive element for driving the adjustment of the positional relationship between the inner rim portion 106L and the rim portion 108L in the z-axis direction by the projection position adjustment mechanism 105L-1 may be, for example, a piezo element, an actuator, or a bimetal, but is not limited thereto. The drive element for driving the adjustment of the positional relationship between the HOE 103L and the inner rim portion 106L in the x-axis direction by the projection position adjustment mechanism 105L-2 may also be, for example, a piezo element, an actuator, or a bimetal, but is not limited thereto.

The projection position adjustment mechanism 105L-1 can adjust the positional relationship between the inner rim portion 106L and the rim portion 108L in the z-axis direction on the basis of, for example, a change in the position of the display device 100 detected by one, two, three, or all four of the sensors 104L, 104R, 104C, and 104T. Furthermore, the projection position adjustment mechanism 105L-1 may adjust the positional relationship on the basis of a change in the position and the line of sight detected by the line-of-sight detection device 107L. The projection position adjustment mechanism 105L-2 can adjust the positional relationship between the HOE 103L and the inner rim portion 106L in the x-axis direction on the basis of, for example, a change in the position of the display device 100 detected by one, two, three, or all four of the sensors 104L, 104R, 104C, and 104T. Furthermore, the projection position adjustment mechanism 105L-2 may adjust the positional relationship on the basis of a change in the position and the line of sight detected by the line-of-sight detection device 107L.

The projection position adjustment mechanisms 105R-1 and 105R-2 adjust the projection position of the video display light projected on the right eye. The adjustment may be performed similarly to the projection position adjustment mechanisms 105L-1 and 105L-2.

(Control Unit and Storage Unit)

This will be described with reference to FIG. 21. The display device 100 includes a control unit 112. As illustrated in FIG. 21 which is a block diagram illustrating main components of the display device 100, the control unit 112 includes an image control unit 181, a projection position control unit 182, and a line-of-sight correction unit 183.

The image control unit 181 controls projection of image display light by the image display unit. The image control unit 181 drives, for example, the light source units 101L and 101R, particularly, the laser light source and the scanning mirror included in these light source units to output the image display light. The image control unit 181 can acquire image data stored in a storage unit 184, for example, and can cause the light source units 101L and 101R to output the image display light on the basis of the image data. The image control unit 181 may correct the image data on the basis of the change in the position of the display device 100 with respect to the head detected by the sensor 104. The image control unit 181 may cause the light source units 101L and 101R to output the image display light on the basis of the image data after correction. That is, the display device 100 may correct the image on the basis of a change in position detected by a sensor that detects a change in position of the head-mounted display device with respect to the head.

The projection position control unit 182 controls the projection position adjustment mechanisms 105L-1, 105L-2, 105R-1, and 105R-2, whereby the projection position of the image display light can be controlled. For example, the projection position control unit 182 can drive one to four of the projection position adjustment mechanisms 105L-1, 105L-2, 105R-1, and 105R-2 on the basis of the line of sight detected by the line-of-sight detection devices 107L and 107R to adjust the projection position of the image display light. For example, the projection position of the image display light can be adjusted so as to follow the line of sight. The projection position control unit 182 may drive one to four of the projection position adjustment mechanisms 105L-1, 105L-2, 105R-1, and 105R-2 on the basis of the line of sight after correction by the line-of-sight correction unit 183 described later to adjust the projection position of the image display light. For example, the projection position of the image display light can be adjusted so as to follow the line of sight after correction. The projection position control unit 182 may adjust the projection position of the image display light by driving one to four of the projection position adjustment mechanisms 105L-1, 105L-2, 105R-1, and 105R-2 on the basis of data (hereinafter also referred to as "displacement data") regarding a change in the position of the display device 100 with respect to the head detected by one to four of the sensors 104L, 104R, 104C, and 104T.

For example, the projection position control unit 182 can calculate a position adjustment amount by each projection position adjustment mechanism on the basis of the displacement data and the correction coefficient. The projection position control unit 182 can drive each projection position adjustment mechanism so that the positional relationship is changed by the calculated position adjustment amount. The projection position control unit 182 may acquire a correction coefficient from a correction table stored in advance in the storage unit 184, for example, and use the correction coefficient for calculation of the position adjustment amount. The correction table may include, for example, a plurality of correction coefficients, and the projection position control unit 182 may select a predetermined correction coefficient according to the displacement data from among the plurality of correction coefficients. Furthermore, the correction table may be provided for each projection position adjustment mechanism, for example. The correction table may be provided in advance in the display device 100, or may be updated according to use of the display device 100 by the user. The accuracy of the projection position control can be improved by selecting or updating the correction table or the correction coefficient. The projection position control unit 182 may use the line of sight detected by the line-of-sight detection device or the line of sight after correction by the line-of-sight correction unit 183 in order to calculate the position adjustment amount.

The line-of-sight correction unit 183 corrects the line of sight detected by the line-of-sight detection devices 107L and 107R on the basis of the displacement data. Thus, the line-of-sight correction unit 183 can identify the line of sight in consideration of the attachment deviation, and the line-of-sight detection accuracy is improved. The correction may be performed on the optical axis of the eyeball, may be performed on the visual axis of the eyeball, or may be performed on another reference axis. The line-of-sight correction unit 183 may also acquire a correction coefficient from a correction table stored in advance in the storage unit 184, for example, and use the correction coefficient for the line-of-sight correction. The correction table may include, for example, a plurality of correction coefficients, and the line-of-sight correction unit 183 may select a predetermined correction coefficient according to the displacement data from among the plurality of correction coefficients. The correction table may be provided in advance in the display device 100, or may be updated according to use of the display device 100 by the user. The accuracy of the line-of-sight correction can be improved by selecting or updating the correction table or the correction coefficient.

The display device 100 may further include the storage unit 184. The storage unit may store data related to the image display light projected by the image display unit, a correction table used for controlling the projection position by a projection position control unit 122, and a correction table used for correcting the line of sight by a line-of-sight correction unit 123.

Note that the embodiments according to the present technology are not limited to the above-described embodiments, and various modifications can be made without departing from the gist of the present technology.

Furthermore, the effects described in the present description are merely examples and are not limited, and other effects may be provided.

Furthermore, the present technology can also have the following configurations.

[1]
A line-of-sight detection device, including:
an imaging element;
an illumination unit that illuminates an eyeball with a plurality of beams of illumination light;
an optical element that guides respective beams of reflected light in a plurality of directions from the eyeball caused by the plurality of beams of illumination light to a direction of the imaging element;
an optical system that causes the imaging element to non-selectively receive the beams of reflected light in the plurality of directions from the eyeball; and
a calculation unit that converts, on the basis of the beams of reflected light in the plurality of directions from the eyeball received by the imaging element, the beams of reflected light into information of eyeball movement and/or positional information of a pupil.

[2]
The line-of-sight detection device according to [1], in which the imaging element has an event-driven function.

[3]
The line-of-sight detection device according to [1] or [2], in which the optical system causes the imaging element to receive the beams of reflected light in the plurality of directions from the eyeball without spatial assignment.

[4]
The line-of-sight detection device according to any one of [1] to [3], in which
the optical element includes a plurality of optical elements, and
each of the plurality of optical elements guides respective beams of reflected light in the plurality of directions from the eyeball to the direction of the imaging element.

[5]
The line-of-sight detection device according to any one of [1] to [4], in which elements, and
at least one optical element of the plurality of optical elements is a diffraction grating.

[6]
The line-of-sight detection device according to any one of [1] to [5], in which a beam of reflected light in one of the plurality of directions from the eyeball is a beam of light from an optical axis of the eyeball.

[7]
The line-of-sight detection device according to any one of [1] to [6], in which
the optical element includes a plurality of optical elements,
the plurality of optical elements includes a first optical element and a second optical element, and
a difference between reflectance of the first optical element and reflectance of the second optical element is 50% or more.

[8]
The line-of-sight detection device according to any one of [1] to [7], in which
the optical element includes a plurality of optical elements,
the plurality of optical elements includes a first optical element and a second optical element, and
a difference between diffraction efficiency of the first optical element and diffraction efficiency of the second optical element is 50% or more.

[9]
The line-of-sight detection device according to any one of [1] to [8], in which
an amount of light reaching the imaging element of a beam of reflected light from an optical axis of the eyeball among the beams of reflected light in the plurality of directions from the eyeball, is larger than an amount of light reaching the imaging element of a beam of reflected light other than the beam of reflected light from the optical axis of the eyeball among the beams of reflected light in the plurality of directions from the eyeball.

[10]

The line-of-sight detection device according to any one of [1] to [9], further including
at least one of a polarizing plate, an ND filter, or a retardation film, in which
by using at least one of the polarizing plate, the ND filter, or the retardation film,
an amount of light reaching the imaging element of a beam of reflected light in at least one direction among the beams of reflected light in the plurality of directions from the eyeball is adjusted.

[11]

The line-of-sight detection device according to any one of [1] to [10], in which
the calculation unit separates information of the beams of reflected light in the plurality of directions from the eyeball received by the imaging element into information of beams of reflected light in respective directions of the plurality of directions from the eyeball received by the imaging element, and
converts, on the basis of each of separated pieces of the information, the each of separated pieces of the information into the information of the eyeball movement and/or the positional information of the pupil.

[12]

The line-of-sight detection device according to any one of [1] to [11], in which
the optical element generates a difference in an amount of light reaching the imaging element of beams of reflected light in at least two directions among the beams of reflected light in the plurality of directions from the eyeball, and
the calculation unit separates information of the beams of reflected light in the at least two directions received by the imaging element into information of beams of reflected light in respective directions of the at least two directions according to the difference in the amount of light, and
converts, on the basis of at least two separated pieces of the information, the at least two separated pieces of the information into the information of the eyeball movement and/or the positional information of the pupil.

[13]

The line-of-sight detection device according to any one of [1] to [12], in which
the optical element generates a difference in aberration of beams of reflected light in at least two directions among the beams of reflected light in the plurality of directions from the eyeball,
the calculation unit includes a low-pass filter and a high-pass filter and
performs Fourier transform on information of beams of reflected light in at least two directions received by the imaging element,
separates the information of the beams of reflected light in the at least two directions into information of beams of reflected light in respective directions of the at least two directions according to the difference in the aberration using the low-pass filter and the high-pass filter, and
converts, on the basis of at least two separated pieces of the information, the at least two separated pieces of the information into the information of the eyeball movement and/or the positional information of the pupil.

[14]

The line-of-sight detection device according to any one of [1] to [13], in which
the calculation unit acquires a point group in a time direction by using each of pieces of information of beams of reflected light in at least two directions among pieces of information of the beams of reflected light in the plurality of directions from the eyeball received by the imaging element, and generates at least two optical flows,
separates the information of the beams of reflected light in the at least two directions into information of beams of reflected light in respective directions of the at least two directions according to a difference between the at least two optical flows, and
converts, on the basis of at least two separated pieces of the information, the at least two separated pieces of the information into the information of the eyeball movement and/or the positional information of the pupil.

[15]

The line-of-sight detection device according to any one of [1] to [14], in which
the calculation unit separates information of the beams of reflected light in the plurality of directions from the eyeball received by the imaging element into information of beams of reflected light in respective directions of the plurality of directions from the eyeball received by the imaging element by using a deep neural network, and
converts, on the basis of each of separated pieces of the information, the each of separated pieces of the information into the information of the eyeball movement and/or the positional information of the pupil.

[16]

The line-of-sight detection device according to [1], in which the imaging element is a CMOS image sensor.

[17]

The line-of-sight detection device according to [16], in which
the calculation unit includes a high-pass filter,
converts information of the beams of reflected light in the plurality of directions from the eyeball received by the CMOS image sensor into edge information by using the high-pass filter,
separates the information of the beams of reflected light in the plurality of directions from the eyeball received by the CMOS image sensor into information of beams of reflected light in respective directions of the plurality of directions from the eyeball received by the CMOS image sensor by using the edge information, and
converts, on the basis of each of separated pieces of the information, the each of separated pieces of the information into the information of the eyeball movement and/or the positional information of the pupil.

[18]

A display device including at least the line-of-sight detection device according to any one of [1] to [17].

REFERENCE SIGNS LIST

1 Dynamic vision sensor (DVS)
4 Substrate
7 LED (illumination unit)
11 Camera (CMOS image sensor)
41 Purkinje image
42 Central portion of pupil
43 Boundary portion (edge portion) between pupil and iris 44 Boundary portion (edge portion) between iris and sclera
45 Pupil
46 Iris
47 Sclera
51, 55, 57, 59, 513 HOE (Holographic Optical Element) grating (hologram diffraction grating)
61, 65, 67, 69, 613 HOE (Holographic Optical Element) mirror (hologram mirror)
87-1, 87-2 Polarizing plate
97 Retardation film
100 Display device
500, 500-1, 500-2 Eyeball
1001, 1005, 1007, 1009, 1013 Line-of-sight detection device
L1-1, L5-1, L9-1, L13-1 First beam of reflected light from eyeball
L1-2, L5-2, L9-2, L13-2 Second beam of reflected light from eyeball
L1-1a, L5-1a, L9-1a, L13-1a First beam of deflected light
L1-2a, L5-2a, L9-2a, L13-2a Second beam of deflected light
L7-1 First beam of reflected light (first beam of polarized light) from eyeball
L7-1a First beam of deflected light (first beam of polarized light)
L7-2 Second beam of reflected light (second beam of polarized light) from eyeball
L7-2a Second beam of deflected light (second beam of polarized light)
m1, m2, m3, m4, m5 Left boundary portion (left edge portion) between pupil and iris
n1, n2, n3, n4, n5 Right boundary portion (right edge portion) between pupil and iris

The invention claimed is:

1. A line-of-sight detection device, comprising:
an imaging element;
an illumination unit configured to illuminate an eyeball with a plurality of beams of illumination light;
an optical element configured to guide a plurality of beams of reflected light to a direction of the imaging element, wherein
the plurality of beams of reflected light includes the plurality of beams of illumination light reflected in a plurality of directions from the eyeball,
the optical element includes a plurality of optical elements,
a first optical element of the plurality of optical elements has:
a substantial difference in diffraction efficiency from a diffraction efficiency of a second optical element of the plurality of optical elements, or
a substantial difference in reflectance amount from a reflectance amount of the second optical element, and
each of the plurality of optical elements is configured to guide a respective beam of reflected light of the plurality of beams of reflected light in the plurality of directions from the eyeball to the direction of the imaging element;
an optical system configured to cause the imaging element to non-selectively receive the plurality of beams of reflected light in the plurality of directions from the eyeball; and
a calculation unit configured to convert, based on the plurality of beams of reflected light in the plurality of directions from the eyeball received by the imaging element, the plurality of beams of reflected light into at least one of information of eyeball movement or positional information of a pupil.

2. The line-of-sight detection device according to claim 1, wherein the imaging element has an event-driven function.

3. The line-of-sight detection device according to claim 1, wherein the optical system is further configured to cause the imaging element to receive the plurality of beams of reflected light in the plurality of directions from the eyeball without spatial assignment.

4. The line-of-sight detection device according to claim 1, wherein
at least one optical element of the plurality of optical elements is a diffraction grating.

5. The line-of-sight detection device according to claim 1, wherein a beam of reflected light of the plurality of beams of reflected light which is reflected in one direction of the plurality of directions from the eyeball is a beam of light from an optical axis of the eyeball.

6. The line-of-sight detection device according to claim 1, wherein
the substantial difference between the reflectance amount of the first optical element and the reflectance amount of the second optical element is 50% or more.

7. The line-of-sight detection device according to claim 1,
the substantial difference between the diffraction efficiency of the first optical element and the diffraction efficiency of the second optical element is 50% or more.

8. The line-of-sight detection device according to claim 1, wherein
the plurality of beams of reflected light includes:
a first beam of reflected light that is reflected from an optical axis of the eyeball, and
a second beam of reflected light that is different from the first beam of the reflected light, and
an amount of light of the first beam of reflected light that reaches the imaging element is larger than an amount of light of the second beam of reflected light that reaches the imaging element.

9. The line-of-sight detection device according to claim 1, further comprising
at least one of a polarizing plate, an ND filter, or a retardation film, wherein
based on the at least one of the polarizing plate, the ND filter, or the retardation film, an amount of light of a first beam of reflected light of the plurality of beams of reflected light is adjustable, and
the first beam of reflected light is reflected in at least one direction of the plurality of directions.

10. The line-of-sight detection device according to claim 1, wherein
the calculation unit is further configured to:
separate information of the plurality of beams of reflected light in the plurality of directions received by the imaging element into information of beams of reflected light in respective directions of the plurality of directions; and
convert, based on the separated information of beams of reflected light in the respective directions, each of the separated information of beams of reflected light in the respective directions into the at least one of information of the eyeball movement or the positional information of the pupil.

11. The line-of-sight detection device according to claim 1, wherein the plurality of beams of reflected light includes:
a first beam of reflected light that is reflected in a first direction of the plurality of directions, and
a second beam of reflected light that is reflected in a second direction of the plurality of directions, wherein the second direction is different from the first direction,
the optical element is further configured to generate a difference in an amount of light of the first beam of reflected light that reaches the imaging element and an amount of light of the second beam of reflected light that reaches the imaging element, and
the calculation unit is further configured to:
separate information of the first beam of reflected light and the second beam of reflected light into first information of the first beam of reflected light that is reflected in the first direction and second information of the second beam of reflected light that is reflected in the second direction; and
convert, based on the first information and the second information, the first information and the second information into the at least one of the information of the eyeball movement or the positional information of the pupil.

12. The line-of-sight detection device according to claim 1, wherein
the plurality of beams of reflected light includes:
a first beam of reflected light that is reflected in a first direction of the plurality of directions, and
a second beam of reflected light that is reflected in a second direction of the plurality of directions, wherein the second direction is different from the first direction,
the optical element that includes the plurality of optical elements is further configured to generate a difference in aberration of the first beam of reflected light and the second beam of reflected light,
the calculation unit includes a low-pass filter and a high-pass filter, and
the calculation unit is further configured to:
perform Fourier transform on information of the first beam of reflected light and information of the second beam of reflected light received by the imaging element;
separate the information of the first beam of reflected light and the information of the second beam of reflected light into first information of the first beam of reflected light that is reflected in the first direction and second information of the second beam of reflected light that is reflected in the second direction-based on the difference in the aberration, wherein the information of the first beam of reflected light and the information of the second beam of reflected light is separated based on the low-pass filter and the high-pass filter; and
convert, based on the first information and the second information, the first information and the second information into the at least one of the information of the eyeball movement or the positional information of the pupil.

13. The line-of-sight detection device according to claim 1, wherein
the calculation unit is further configured to:
acquire a point group in a time direction based on each of pieces of information of beams of reflected light in at least two directions among pieces of information of the beams of reflected light in the plurality of directions;
generate at least two optical flows;
separate the information of the beams of reflected light in the at least two directions into information of beams of reflected light in respective directions of the at least two directions based on a difference between the at least two optical flows; and
convert, based on the separated information of the beams of reflected light in the respective directions of the at least two directions, the separated information of the beams of reflected light in the respective directions of the at least two directions into the at least one of the information of the eyeball movement or the positional information of the pupil.

14. The line-of-sight detection device according to claim 1, wherein
the calculation unit is further configured to:
separate information of the plurality of beams of reflected light in the plurality of directions received by the imaging element into information of beams of reflected light in respective directions of the plurality of directions based on a deep neural network; and
convert, based on the separated information of the beams of reflected light in the respective directions of the plurality of directions, the separated information of the beams of reflected light in the respective directions of the plurality of directions into the at least one of the information of the eyeball movement or the positional information of the pupil.

15. The line-of-sight detection device according to claim 1, wherein the imaging element is a CMOS image sensor.

16. The line-of-sight detection device according to claim 15,
wherein
the calculation unit includes a high-pass filter,
the calculation unit is further configured to:
convert information of the plurality of beams of reflected light in the plurality of directions received by the CMOS image sensor into edge information based on the high-pass filter;
separate the information of the plurality of beams of reflected light in the plurality of directions into information of beams of reflected light in respective directions of the plurality of directions based on the edge information; and
convert, based on the separated information, the separated information into the at least one of the information of the eyeball movement or the positional information of the pupil.

17. A display device, comprising:
a line-of-sight detection device comprising:
an imaging element;
an illumination unit configured to illuminate an eyeball with a plurality of beams of illumination light;
an optical element configured to guide a plurality of beams of reflected light to a direction of the imaging element, wherein
the plurality of beams of reflected light includes the plurality of beams of illumination light reflected in a plurality of directions from the eyeball,
the optical element includes a plurality of optical elements,
a first optical element of the plurality of optical elements has:
a substantial difference in diffraction efficiency from a diffraction efficiency of a second optical element of the plurality of optical elements, or a substantial difference in reflectance amount from a reflectance amount of the second optical element, and each of the plurality of optical elements is configured to guide a respective beam of reflected light of the plurality of beams of reflected light in the plurality of directions from the eyeball to the direction of the imaging element;

an optical system configured to cause the imaging element to non-selectively receive the plurality of beams of reflected light in the plurality of directions from the eyeball; and a calculation unit configured to convert, based on the plurality of beams of reflected light in the plurality of directions from the eyeball received by the imaging element, the plurality of beams of reflected light into at least one of information of eyeball movement or positional information of a pupil.

18. A line-of-sight detection device, comprising:

an imaging element;

an illumination unit configured to illuminate an eyeball with a plurality of beams of illumination light;

an optical element configured to guide a plurality of beams of reflected light to a direction of the imaging element, wherein the plurality of beams of reflected light includes the plurality of beams of illumination light reflected in a plurality of directions from the eyeball, the optical element includes a plurality of optical elements, the plurality of optical elements includes a first optical element and a second optical element, and a difference between reflectance of the first optical element and reflectance of the second optical element is 50% or more;

an optical system configured to cause the imaging element to non-selectively receive the plurality of beams of reflected light in the plurality of directions from the eyeball; and a calculation unit configured to convert, based on the plurality of beams of reflected light in the plurality of directions from the eyeball received by the imaging element, the plurality of beams of reflected light into at least one of information of eyeball movement or positional information of a pupil.

19. A line-of-sight detection device, comprising:

an imaging element;

an illumination unit configured to illuminate an eyeball with a plurality of beams of illumination light;

an optical element configured to guide a plurality of beams of reflected light to a direction of the imaging element, wherein the plurality of beams of reflected light includes the plurality of beams of illumination light reflected in a plurality of directions from the eyeball, the optical element includes a plurality of optical elements, the plurality of optical elements includes a first optical element and a second optical element, and a difference between diffraction efficiency of the first optical element and diffraction efficiency of the second optical element is 50% or more;

an optical system configured to cause the imaging element to non-selectively receive the plurality of beams of reflected light in the plurality of directions from the eyeball; and a calculation unit configured to convert, based on the plurality of beams of reflected light in the plurality of directions from the eyeball received by the imaging element, the plurality of beams of reflected light into at least one of information of eyeball movement or positional information of a pupil.

20. A line-of-sight detection device, comprising:

an imaging element;

an illumination unit configured to illuminate an eyeball with a plurality of beams of illumination light;

an optical element configured to guide a plurality of beams of reflected light to a direction of the imaging element, wherein the plurality of beams of reflected light includes the plurality of beams of illumination light reflected in a plurality of directions from the eyeball;

at least one of a polarizing plate, an ND filter, or a retardation film, wherein based on the at least one of the polarizing plate, the ND filter, or the retardation film, an amount of light of a first beam of reflected light of the plurality of beams of reflected light is adjustable, and the first beam of reflected light is reflected in at least one direction of the plurality of directions;

an optical system configured to cause the imaging element to non-selectively receive the plurality of beams of reflected light in the plurality of directions from the eyeball; and a calculation unit configured to convert, based on the plurality of beams of reflected light in the plurality of directions from the eyeball received by the imaging element, the plurality of beams of reflected light into at least one of information of eyeball movement or positional information of a pupil.

* * * * *